United States Patent
Kwon et al.

(10) Patent No.: US 9,896,662 B2
(45) Date of Patent: Feb. 20, 2018

(54) PROCESS FOR ENHANCING STEM CELL BIOACTIVITY USING TAUROURSODEOXYCHOLIC ACID

(71) Applicants: Pusan National University Industry—University Cooperation Foundation, Busan (KR); AJOU UNIVERSITY INDUSTRY-ACADEMIC COOPERATION FOUNDATION, Gyeonggi-do (KR)

(72) Inventors: Sang Mo Kwon, Gyeonggi-do (KR); Sang Gyu Park, Seoul (KR); Jun Hee Lee, Gyeongsangbuk-do (KR); Jin Gu Cho, Gyeonggi-do (KR)

(73) Assignees: Pusan National University Industry-University Cooperation Foundation (KR); Ajou University Industry-Academic Cooperation Foundation (KR)

( * ) Notice: Subject to any disclaimer, the term of this patent is extended or adjusted under 35 U.S.C. 154(b) by 43 days.

(21) Appl. No.: 14/952,284

(22) Filed: Nov. 25, 2015

(65) Prior Publication Data
US 2016/0186145 A1 Jun. 30, 2016

(30) Foreign Application Priority Data

Nov. 27, 2014 (KR) ........................ 10-2014-0167836

(51) Int. Cl.
| | | |
|---|---|---|
| *C12N 5/071* | (2010.01) | |
| *A61K 35/28* | (2015.01) | |
| *A61K 35/44* | (2015.01) | |
| *A61K 31/575* | (2006.01) | |
| *A61K 35/545* | (2015.01) | |

(52) U.S. Cl.
CPC .......... *C12N 5/0692* (2013.01); *A61K 31/575* (2013.01); *A61K 35/28* (2013.01); *A61K 35/44* (2013.01); *A61K 35/545* (2013.01); *C12N 2501/999* (2013.01)

(58) Field of Classification Search
CPC ............ C12N 5/0692; C12N 2501/999; A61K 35/545; A61K 35/28; A61K 31/575; A61K 35/44
See application file for complete search history.

(56) References Cited

U.S. PATENT DOCUMENTS 8,173,627 B2 5/2012 Yoo

FOREIGN PATENT DOCUMENTS

| JP | 2009-530398 A | 8/2009 |
|---|---|---|
| KR | 10-1280911 B1 | 8/2012 |

OTHER PUBLICATIONS

Cha et al. The role of tauroursodeoxycholic acid on adipogenesis of human adipose-derived stem cells by modulation of ER stress. Biomaterials 35 (2014) 2851-2858.*
Gimble et al. Adipose-Derived Stem Cells for Regenerative Medicine. Circ Res. 2007;100:1249-1260.*
Miharada et al. Dppa5 Improves Hematopoietic Stem Cell Activity by Reducing Endoplasmic Reticulum Stress. Cell Reports 7, 1381-1392, Jun. 12, 2014.*
Burt et al. Embryonic Stem Cells as an Alternate Marrow Donor Source: Engraftment without Graft-Versus-Host Disease. J. Exp. Med. vol. 199, No. 7, Apr. 5, 2004 895-904.*
Nery et al. Human Mesenchymal Stem Cells: From Immunophenotyping by Flow Cytometry to Clinical Applications. Cytometry Part A, 83A: 48-61, 2013.*
What are Progenitor Cells? Boston Children's Hospital. 2017. p. 1 downloaded from http://stemcell.childrenshospital.org/about-stem-cells/adult-somatic-stem-cells-101/what-are-progenitor-cells/.*
Cho et al., "Tauroursodeoxycholic Acid, a Bile Acid, Promotes Blood Vessel Repair by Recruiting Vasculogenic Progenitor Cells", Stem Cells, Oct. 26, 2014, vol. 33:pp. 792-805, AlphaMed Press, Durham, NC.
Xavier et al., "Tauroursodeoxycholic Acid Increases Neural Stem Cell Pool and Neuronal Conversion by Regulating Mitochondria-Cell Cycle Retrograde Signaling", Cell Cycle, Nov. 15, 2014, vol. 13:22, pp. 3576-3589; Taylor & 7rancis Group, LLC, Oxfordshire, UK.

* cited by examiner

*Primary Examiner* — Taeyoon Kim
(74) *Attorney, Agent, or Firm* — Pamela J. Sherwood; Bozicevic, Field & Francis LLP

(57) ABSTRACT

The present invention relates to a process for enhancing stem cell bioactivity using tauroursodeoxycholic acid (TUDCA) or a pharmaceutical acceptable salt thereof.

5 Claims, 31 Drawing Sheets

[Fig. 1a]
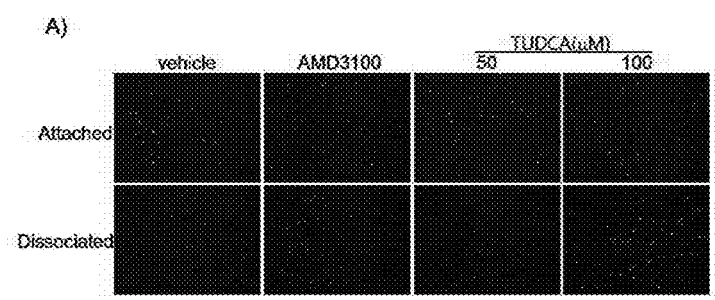
[Fig. 1b]
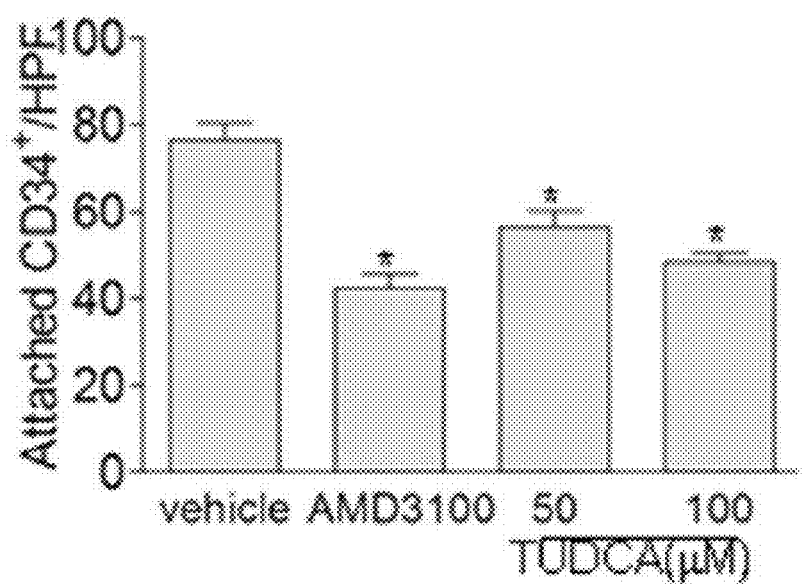

[Fig. 1c]
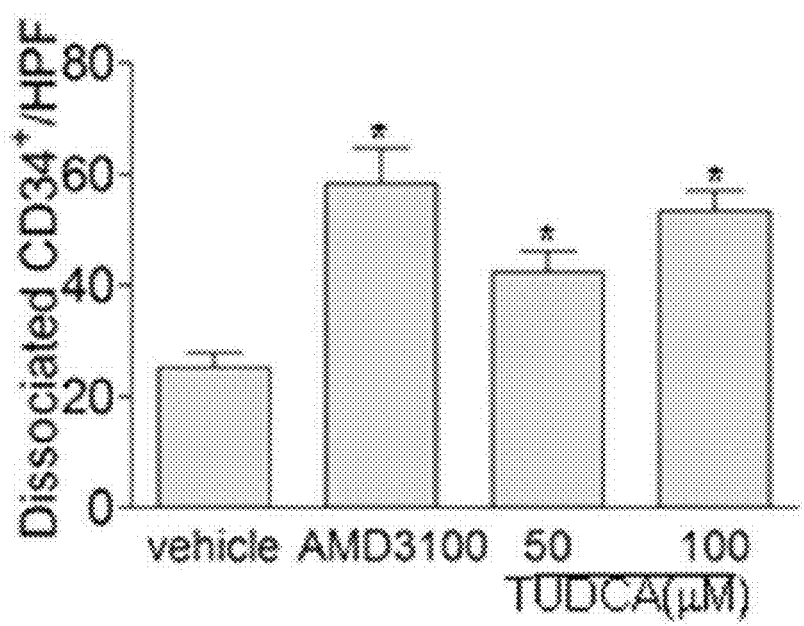

[Fig. 2a]
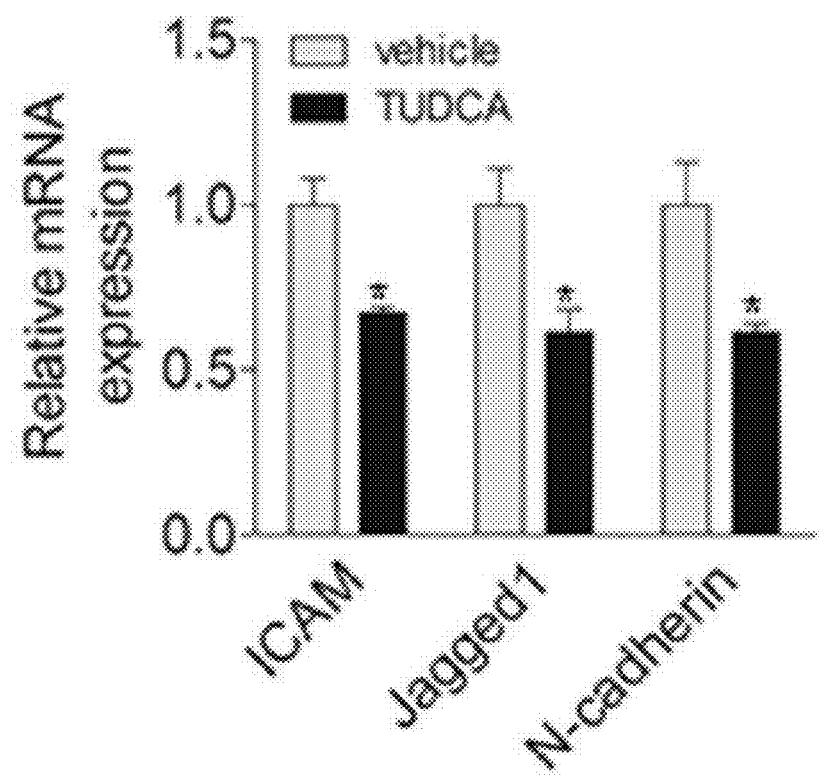

[Fig. 2b]
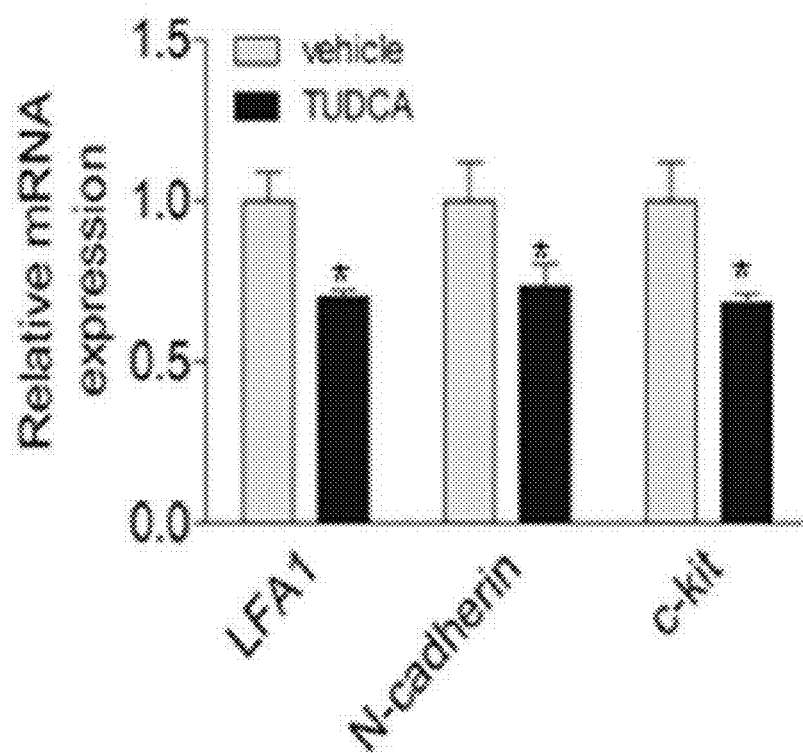

[Fig. 3a]
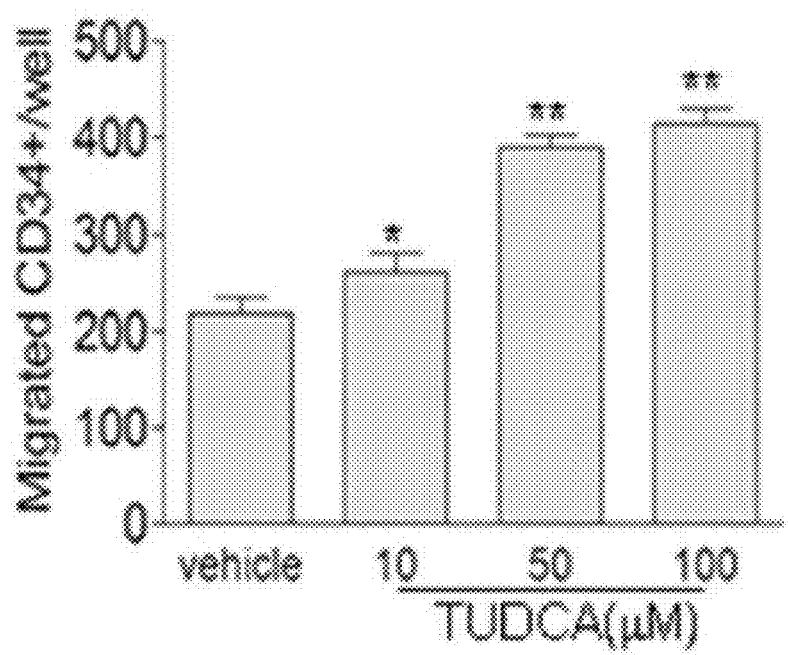

[Fig. 3b]
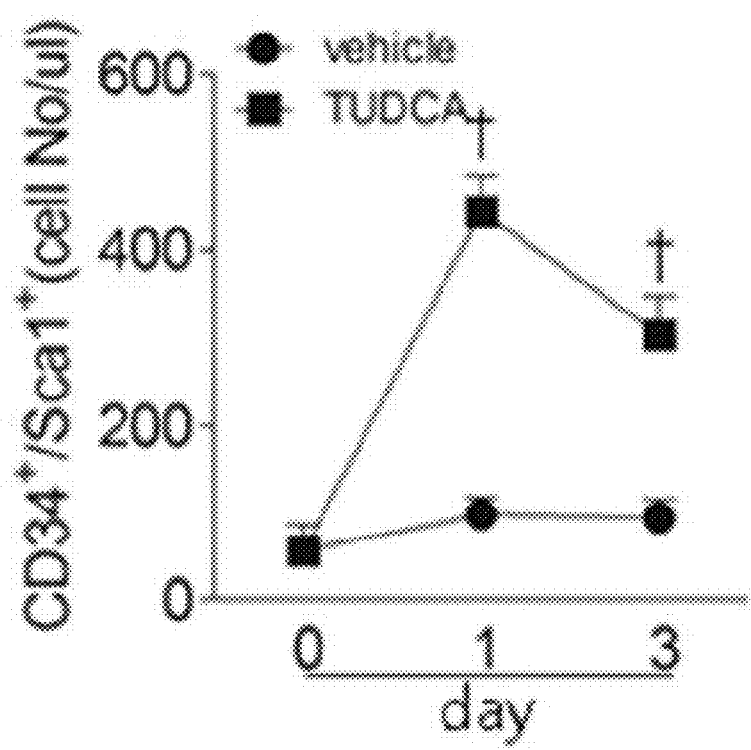

[Fig. 4a]
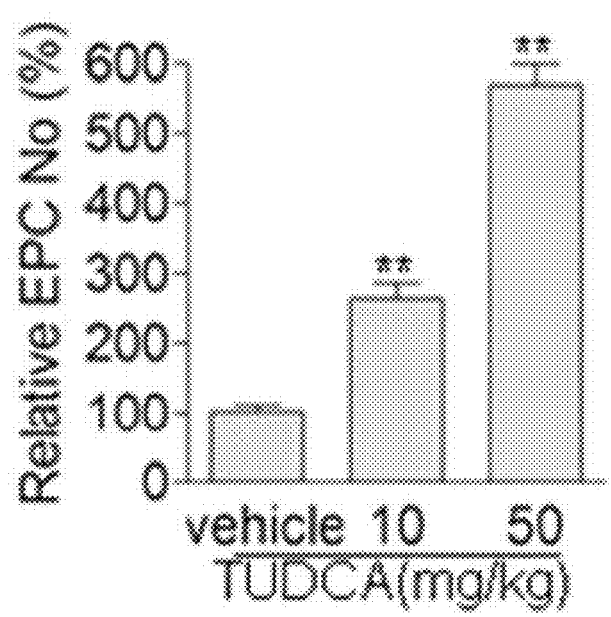

[Fig. 4b]
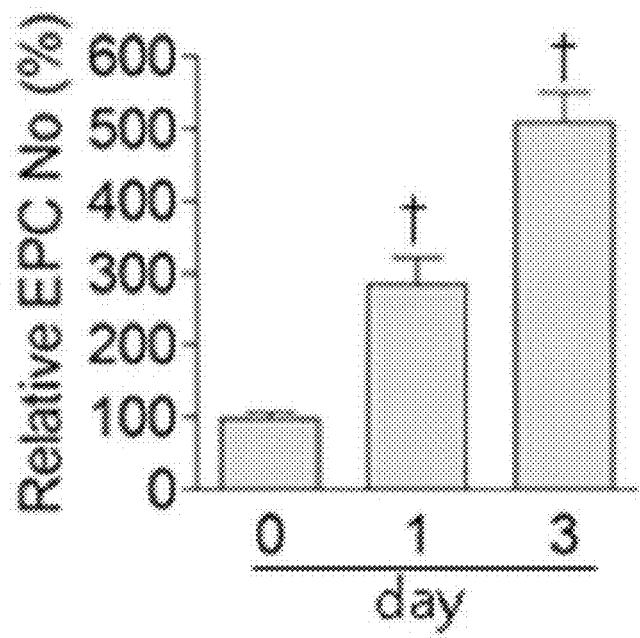
[Fig. 4c]
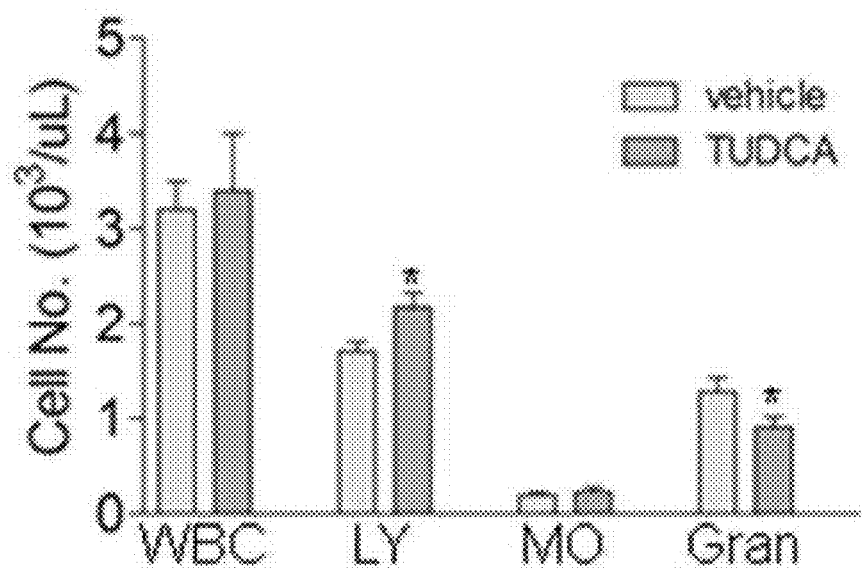

[Fig. 4d]
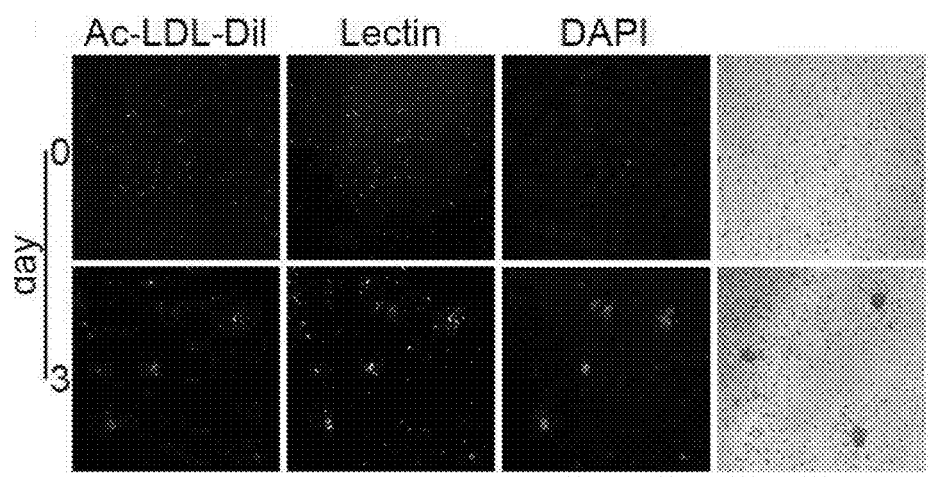
[Fig. 4e]
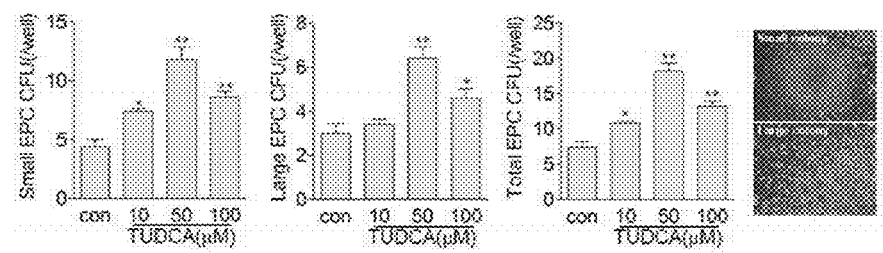

[Fig. 4f]
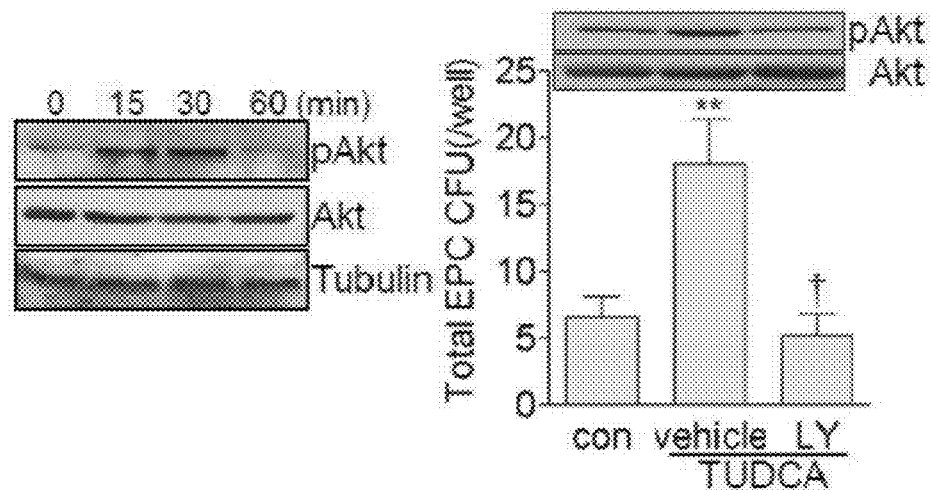
[Fig. 5a]
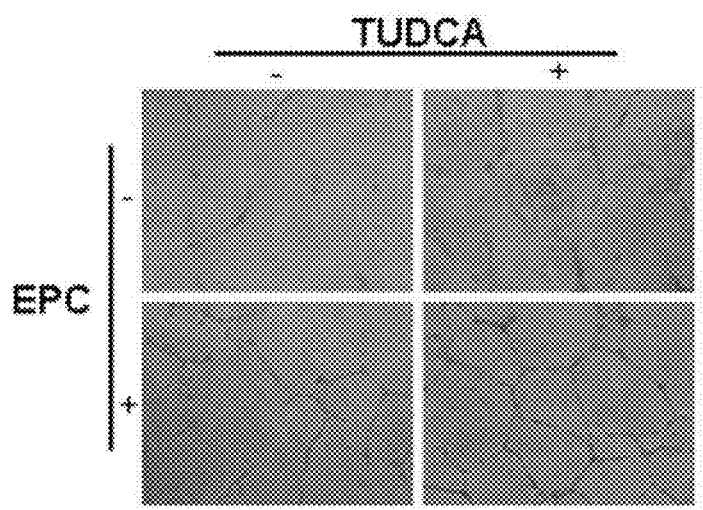

[Fig. 5b]
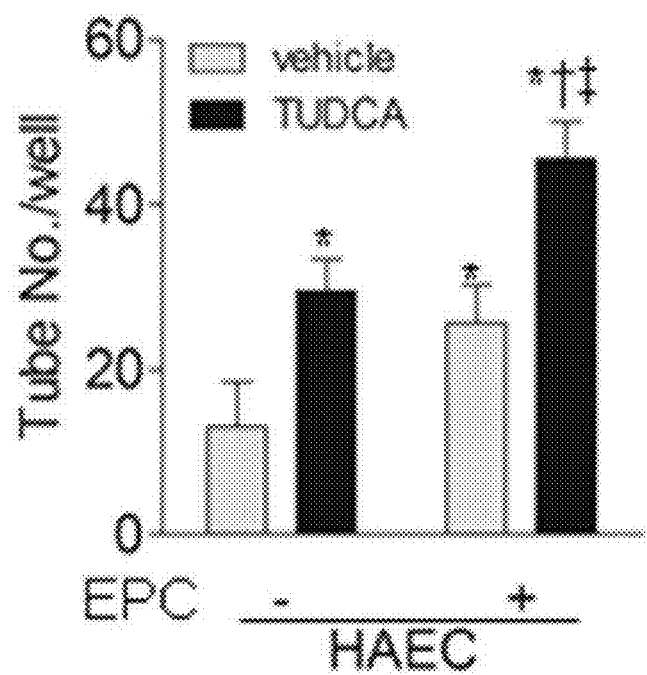
[Fig. 5c]
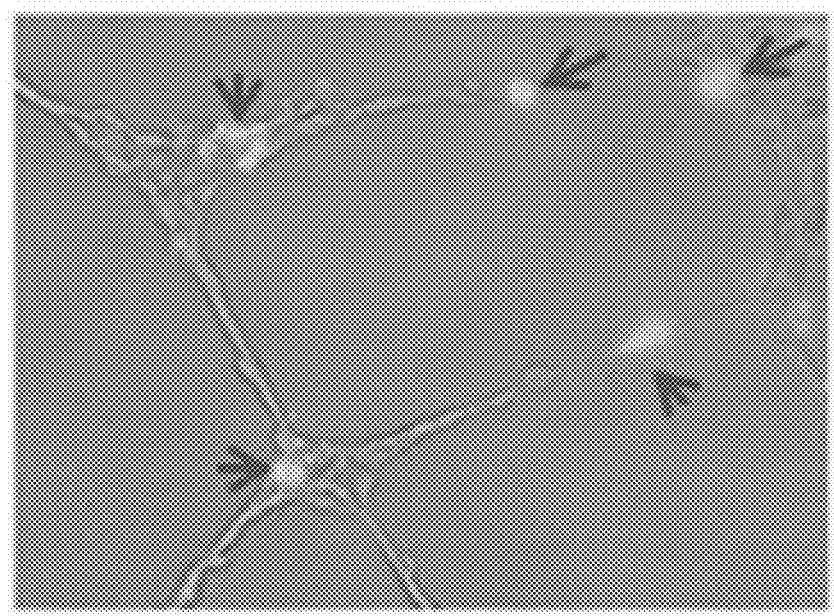

[Fig. 5d]
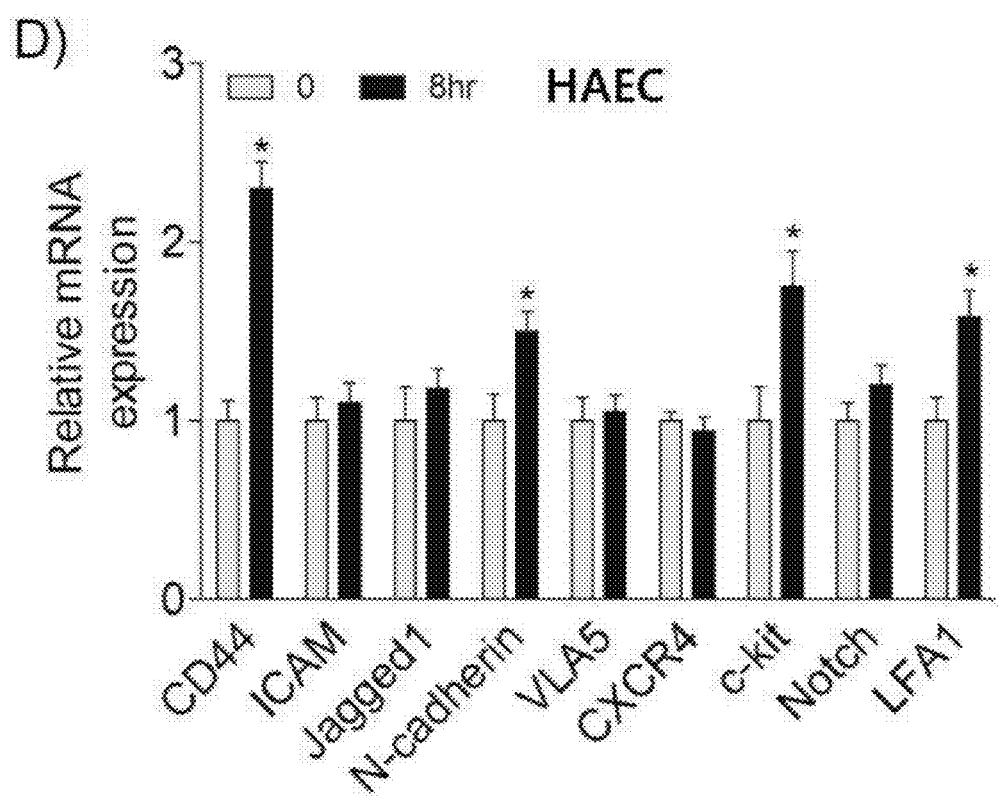

[Fig. 5e]
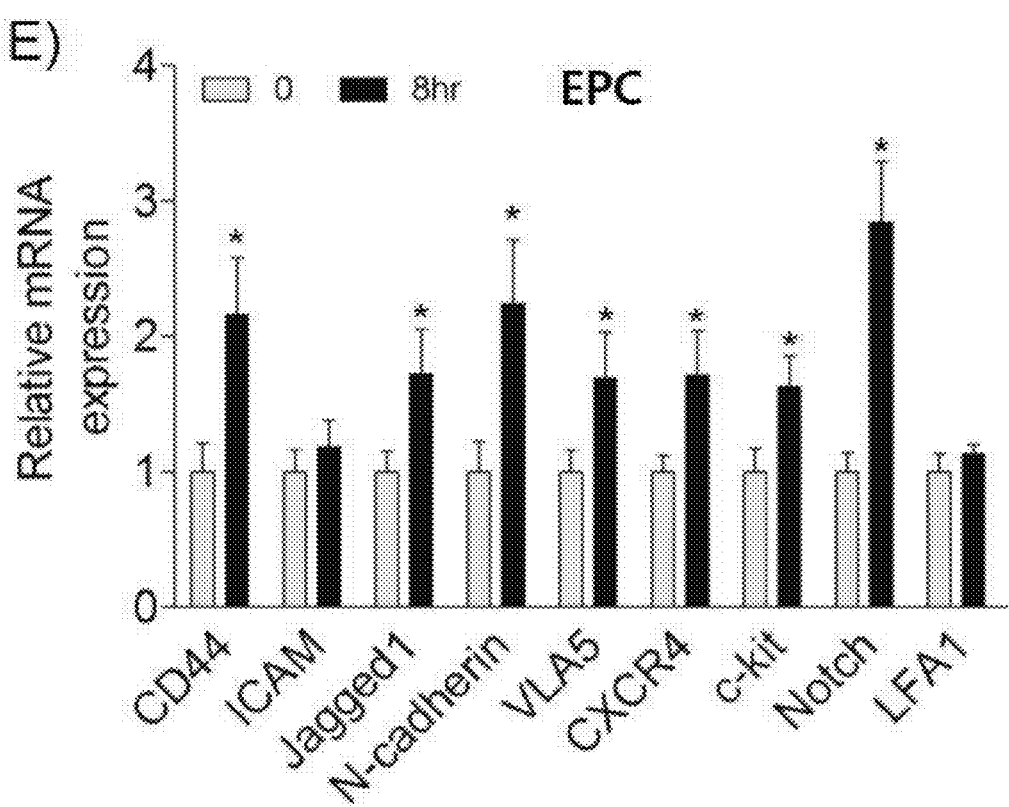

[Fig. 6a]
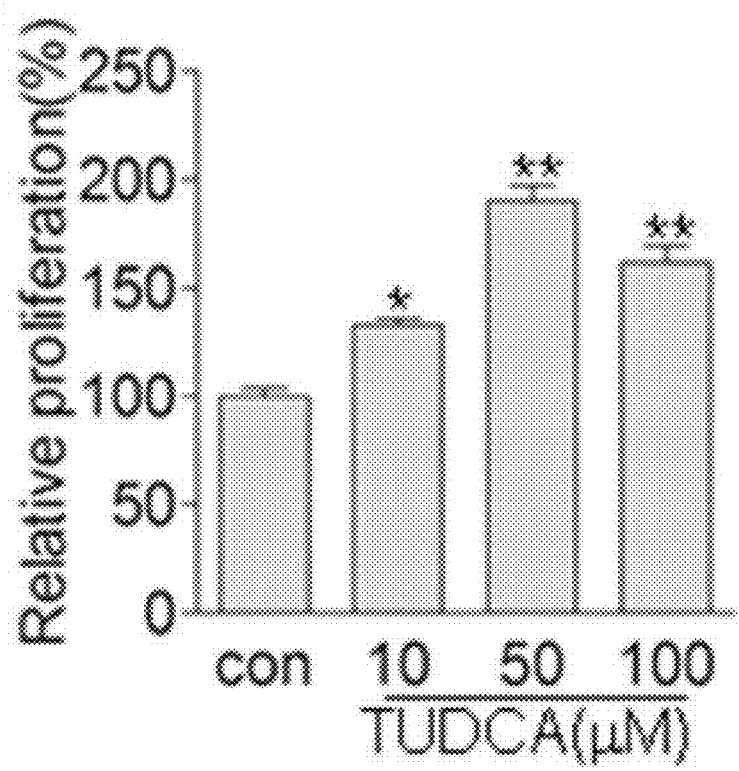

[Fig. 6b]
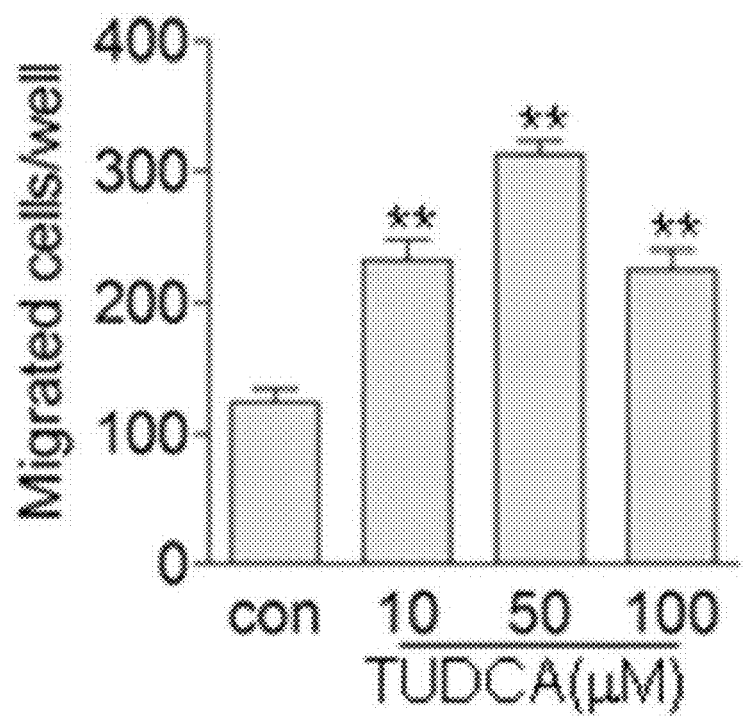

[Fig. 6c]
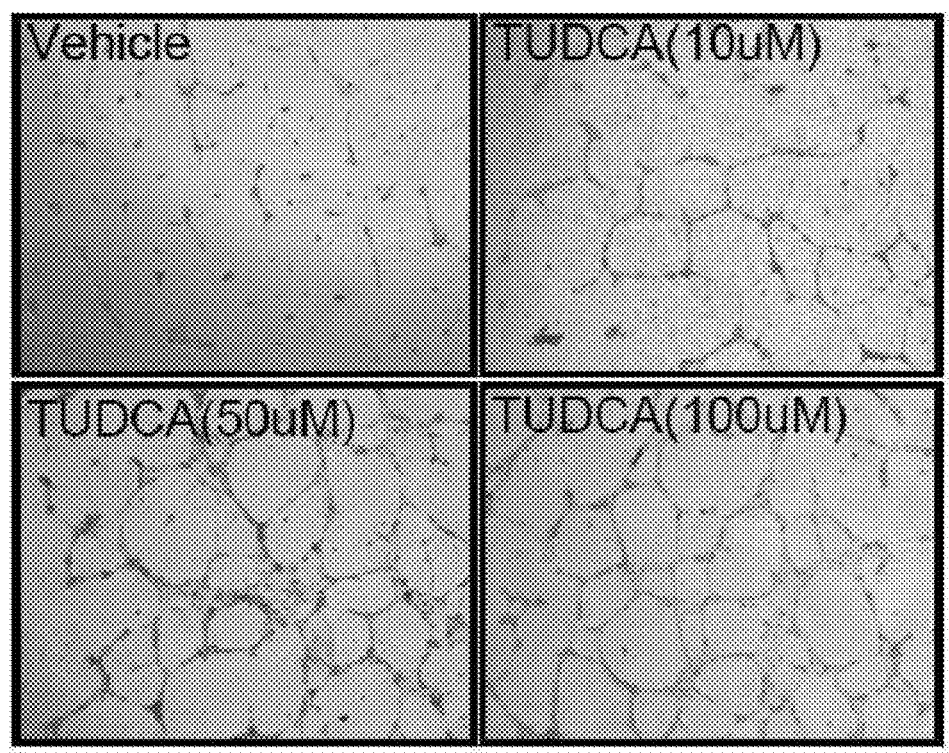

[Fig. 6d]
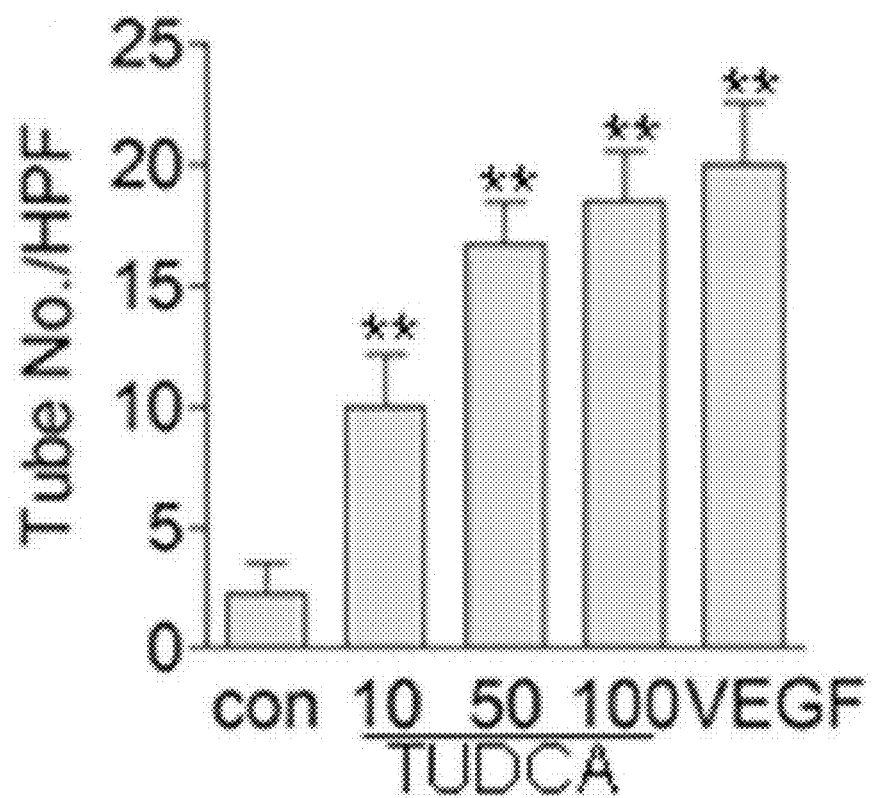
[Fig. 7a]
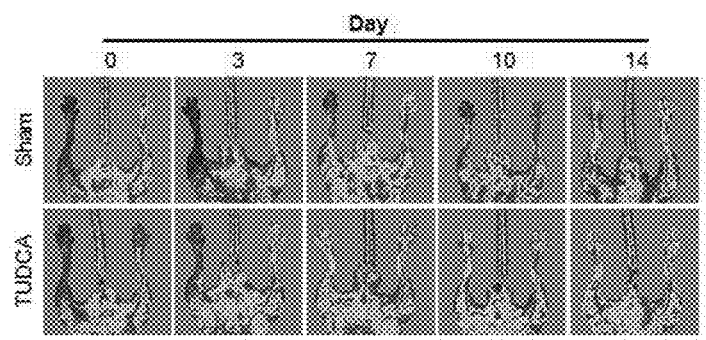

[Fig. 7b]
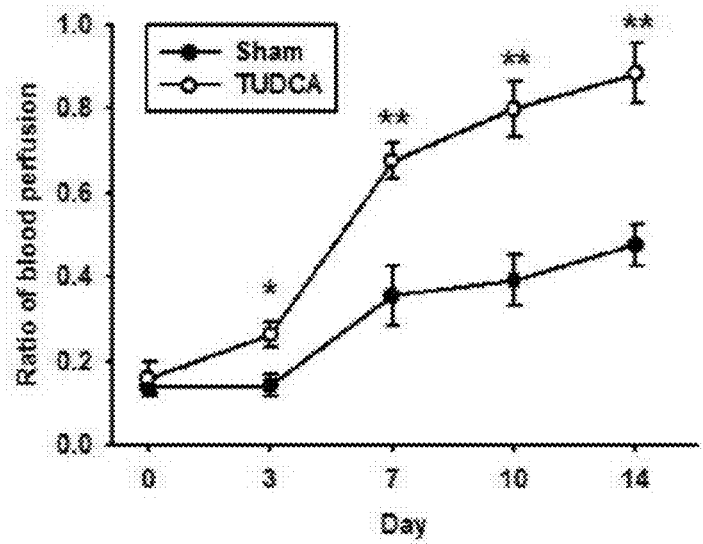
[Fig. 7c]
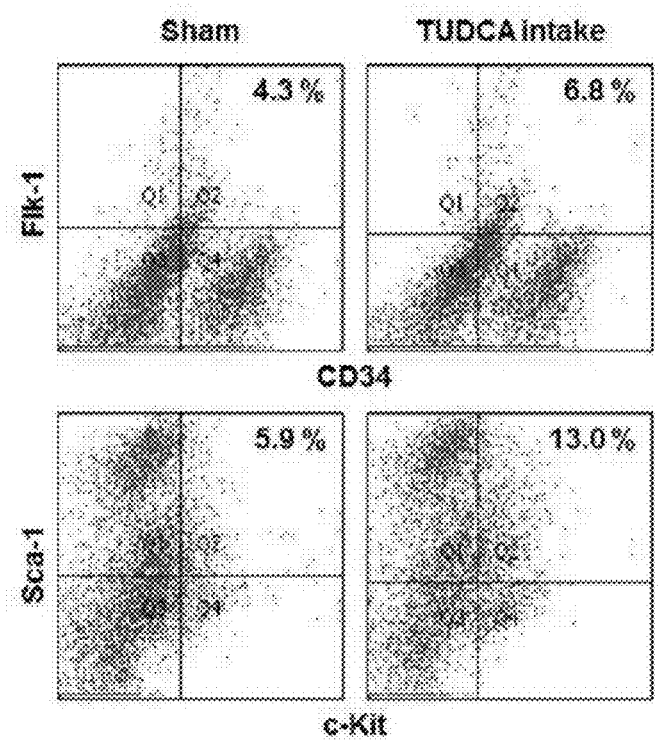

[Fig. 7d]
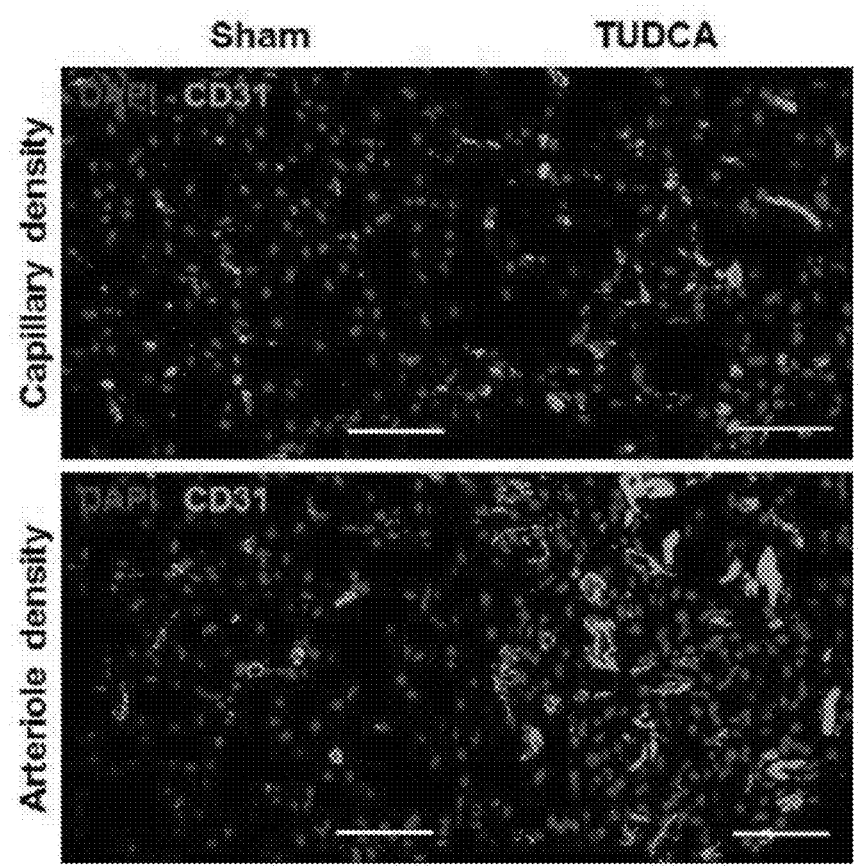

[Fig. 7e]
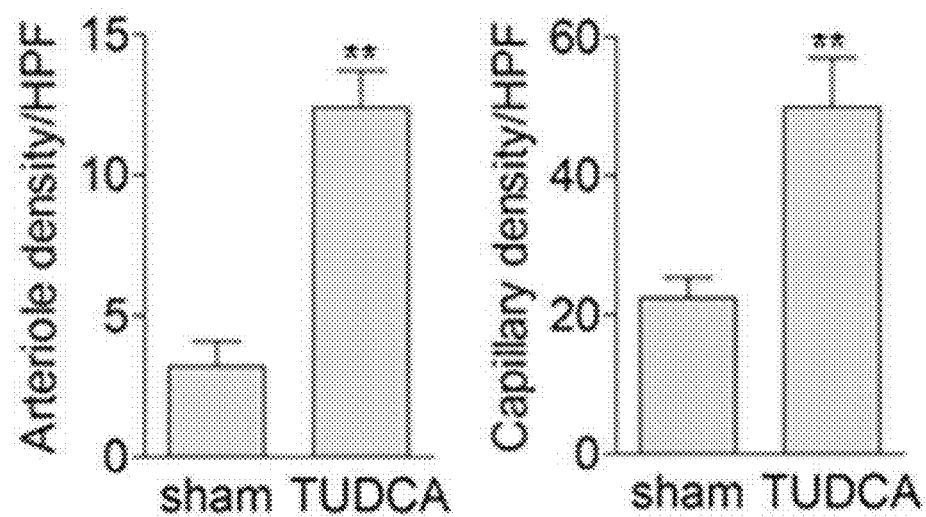
[Fig. 8a]
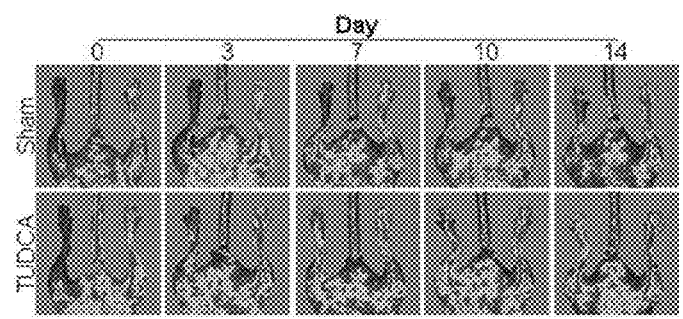

[Fig. 8b]
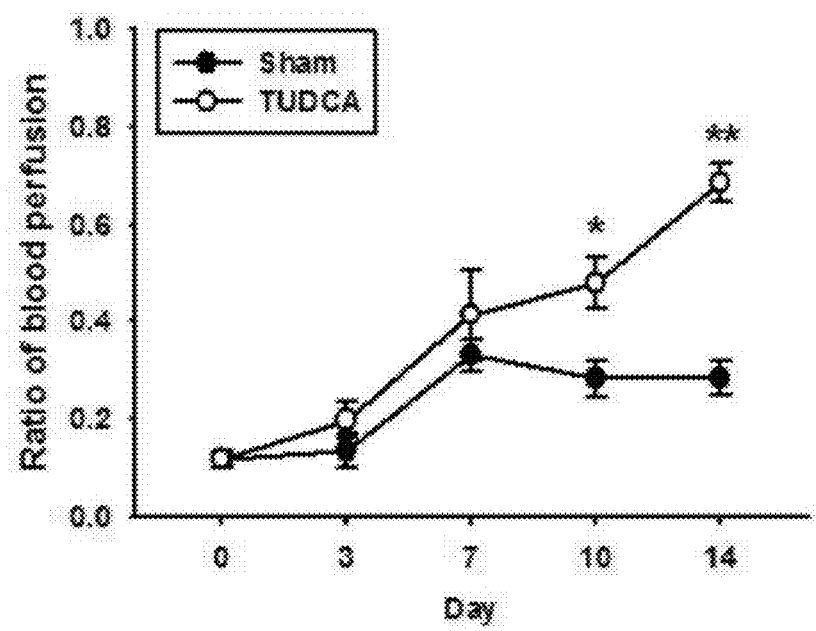

[Fig. 8c]
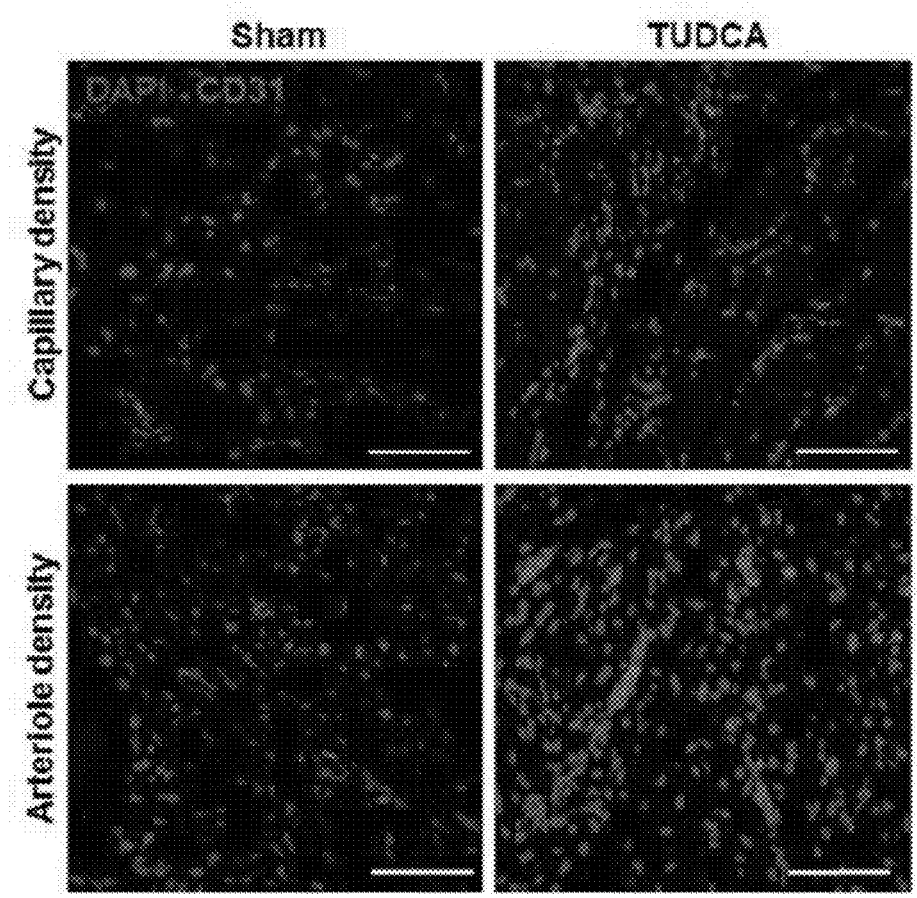

[Fig. 8d]
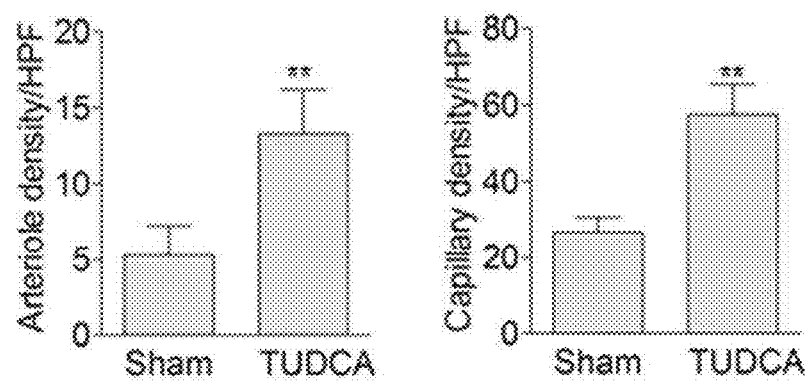
[Fig. 8e]
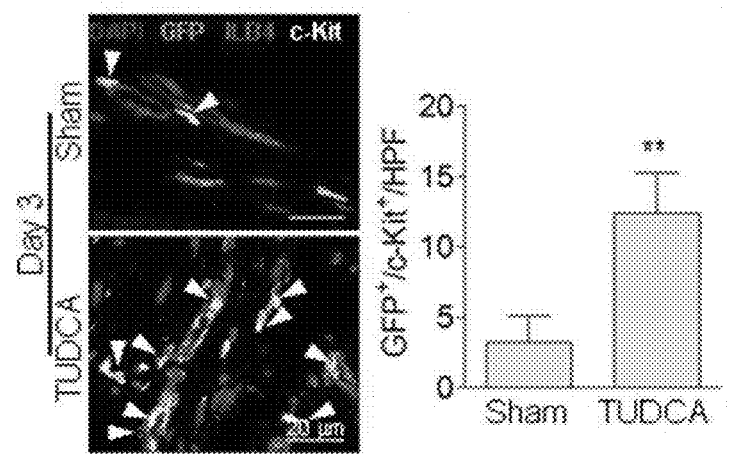

[Fig. 8f]
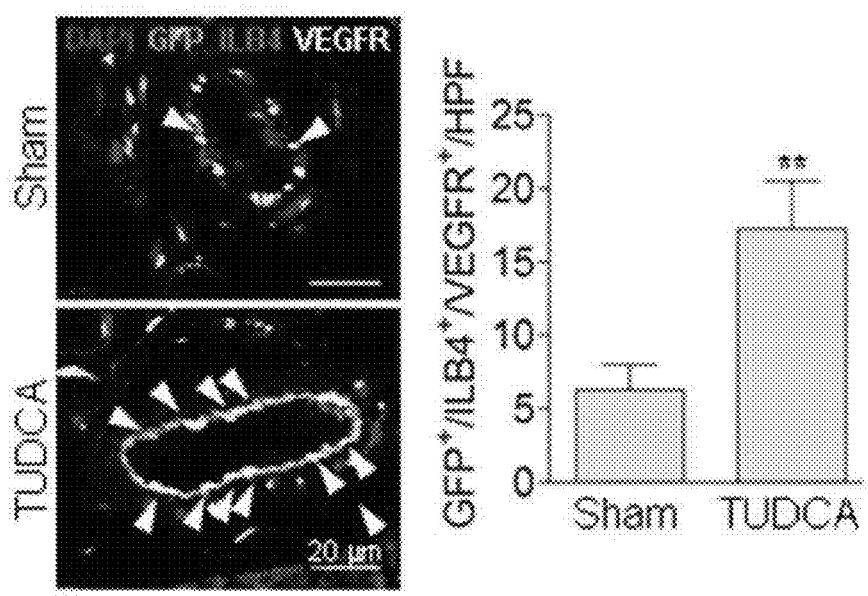
[Fig. 9a]
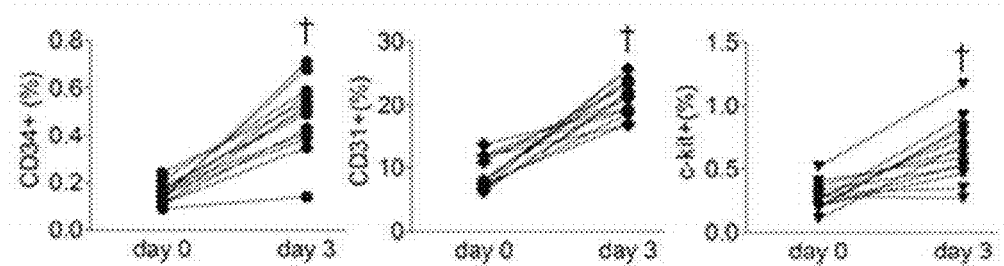

[Fig. 9b]
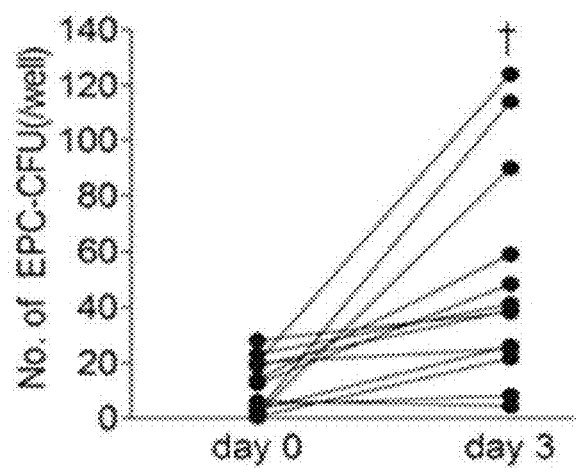
[Fig. 9c]
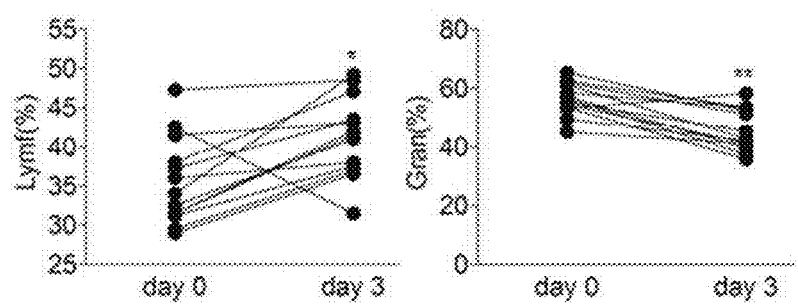

[Fig. 10a]
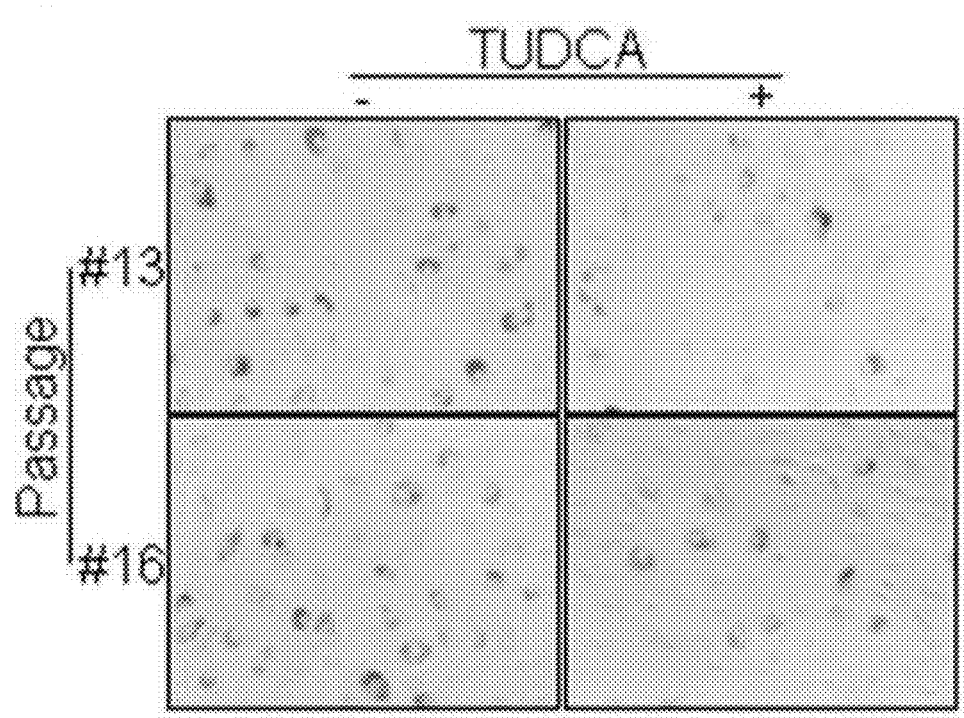

[Fig. 10b]
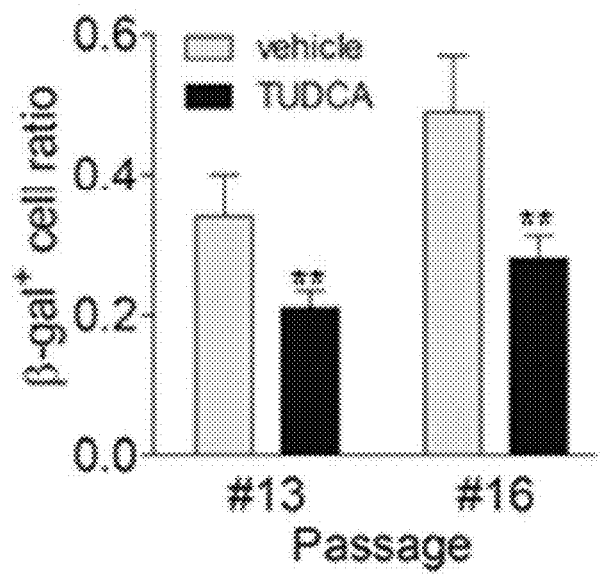
[Fig. 10c]
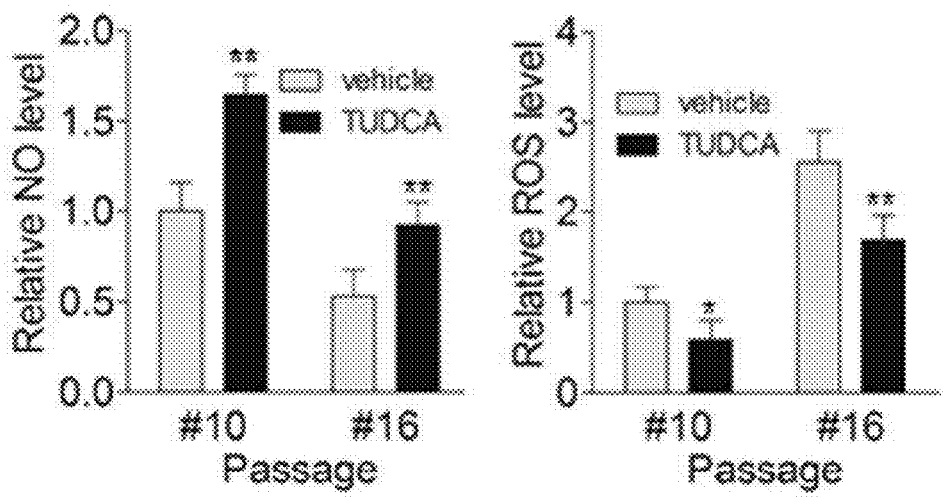

[Fig. 11a]
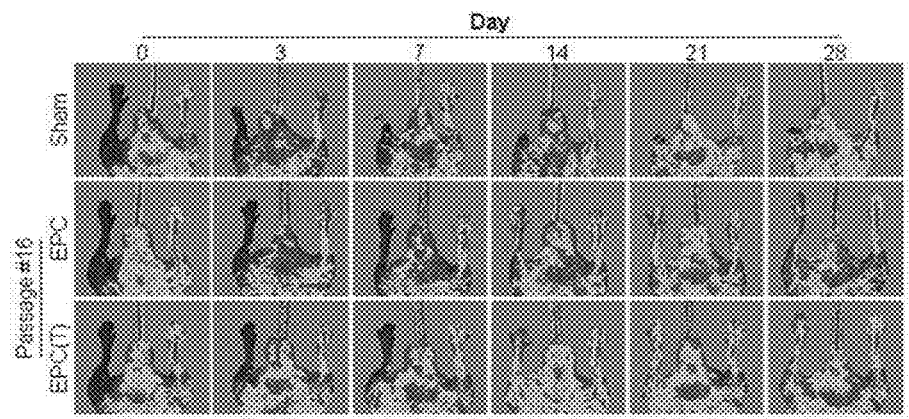
[Fig. 11b]
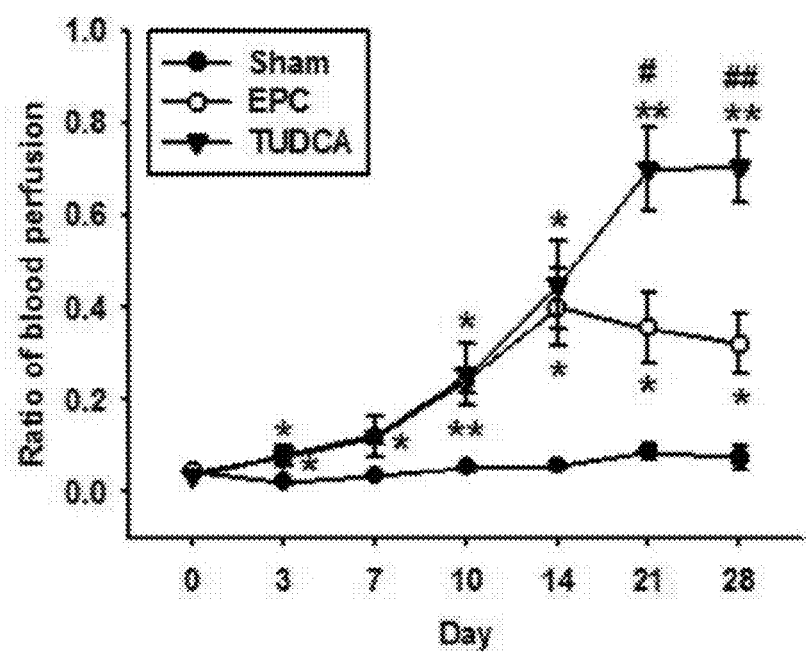

[Fig. 11c]
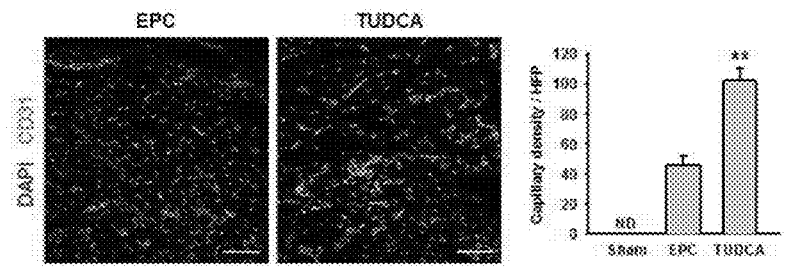
[Fig. 11d]
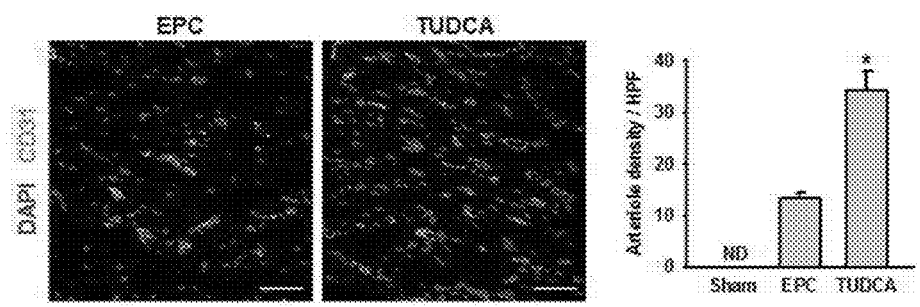
[Fig. 11e]
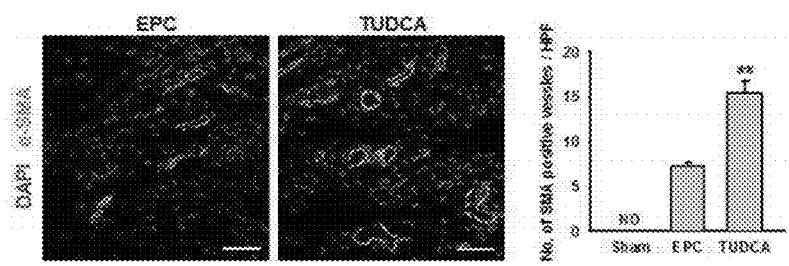

[Fig. 11f]
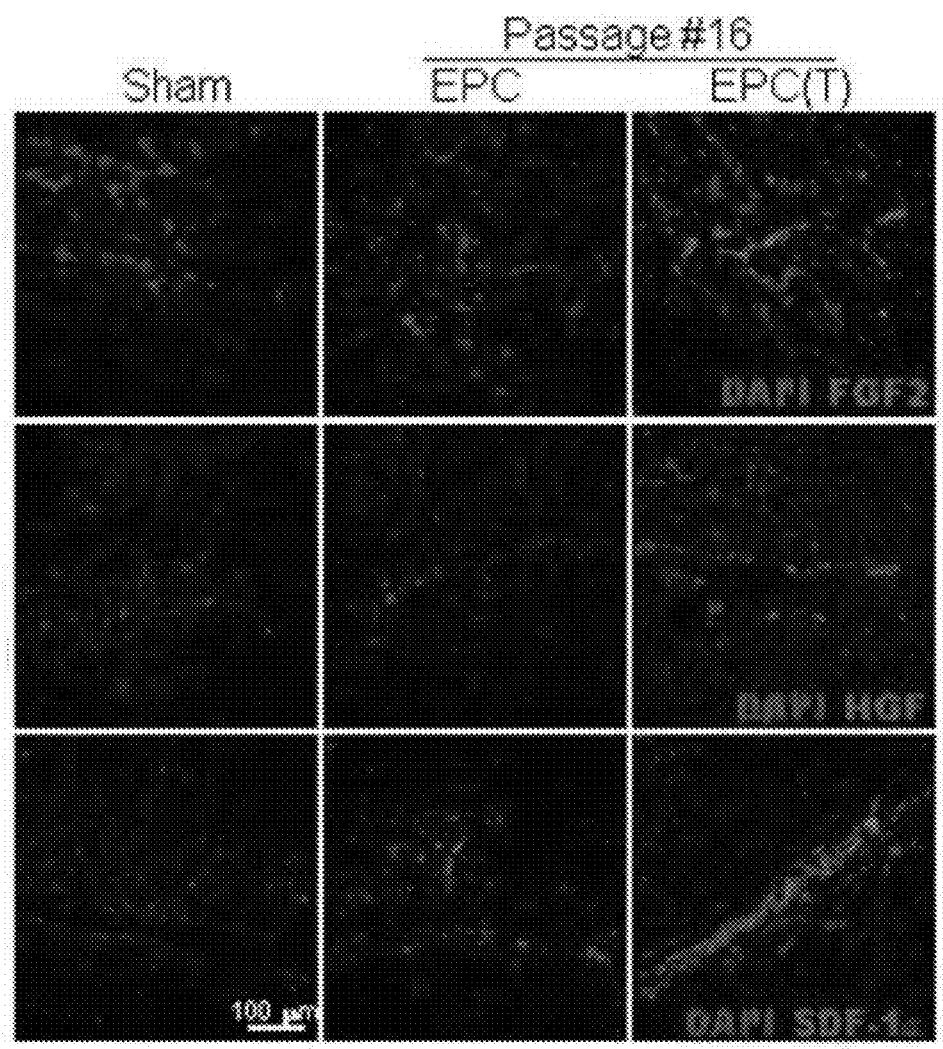

[Fig. 11g]
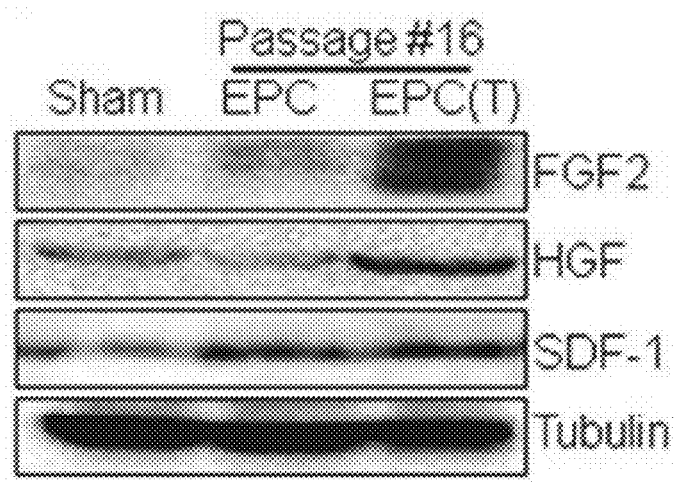

PROCESS FOR ENHANCING STEM CELL BIOACTIVITY USING TAUROURSODEOXYCHOLIC ACID

TECHNICAL FIELD

The present invention relates to a process for enhancing stem cell bioactivity using tauroursodeoxycholic acid (TUDCA).

BACKGROUND ART

Angiogenesis, after birth, occurs by interactions between preexisting endothelial cells and angiogenic stem cells. Angiogenic stem cells include endothelial progenitor cells (EPCs) and endothelial colony forming cells (ECFCs). In the angiogenesis process, preexisting endothelial cells generate new blood vessels through proliferation, migration, infiltration, and vascular tube formation. However, due to various factors, such as chronic exposure to high levels of glucose and cholesterol, smoking, stress, lack of exercise, environmental factors, aging, etc., the activity of preexisting endothelial cells deteriorates, which leads to incomplete angiogenesis and ischemic cardiovascular diseases. Angiogenic stem cells, which are core cells involved in angiogenesis with preexisting endothelial cells, are mainly derived from bone marrow, transported into a site where angiogenesis is required, and differentiated into vascular endothelial cells, to participate in angiogenesis. According to numerous studies, angiogenic stem cells have been found to be critical to angiogenesis after birth. Thus, many studies are ongoing to mobilize angiogenic stem cells from bone marrow to peripheral blood. It was known that various cytokines including granulocyte colony-stimulating factor (GCSF), granulocyte/macrophage colony stimulating factor (GM-CSF), stromal cell-derived factor-1 (SDF-1), or vascular endothelial growth factor (VEGF), are effective in mobilizing angiogenic stem cells from bone marrow. However, these cytokines mobilize not only angiogenic stem cells but also inflammation causing cells. Thus, actual application of these cytokines poses various challenges.

Recently, a cell therapy product using stem cells draw attention as a novel therapy method for repairing damaged tissue or treating refractory diseases. Stem cells have pluripotency and explosive self-replicating capability, and thus have potential of overcoming limits of surgery operations, medicinal therapy, or gene therapy. However, in order for stem cells to be used as a cell therapy product, the following prerequisites should be satisfied. First, a sufficient amount of healthy stem cells should be obtained from patients. Second, when stem cells are transplanted, high transplantation rate should be secured in damaged tissue or a site for treatment. Third, when a stem cell therapy product is transplanted, it should be accurately differentiated into desired cells, organs, or tissue. In order to meet these prerequisites, numerous studies continue to develop in vitro expansion for obtaining a sufficient number of stem cells, various transplantation methods for increasing transplantation efficiency, differentiation induction, etc. Despite these efforts, there are still issues to be resolved in relation with acquisition of stem cells with degraded functions due to various disease risk factors patients have when the stem cells are extracted from the patients, senescence of stem cells occurring upon in vitro expansion, etc.

Meanwhile, tauroursodeoxycholic acid (TUDCA), bill acid, is the taurine conjugate form of ursodeoxycholic acid (UDCA). TUDCA acts as a chemical chaperone to maintain protein stability. According to various reports, it was disclosed that TUDCA has excellent effects as a therapeutic agent for cholestatic liver disease including primary biliary cirrhosis or primary sclerosing cholangitis. Also, TUDCA has been found to have neuroprotective effects by suppressing inflammatory response in ischemic brain diseases. Studies in recent years are proving the effects of TUDCA through mechanisms of preventing apoptosis, such as protection of liver cells, inhibition of neointimal hyperplasia, maintenance of constant sugar, etc. Further, various studies are conducted to treat various refractory diseases including Huntington's disease, Parkinson's disease, and stroke. TUDCA for cells has great effects in preventing apoptosis. Particularly, TUDCA controls the apoptosis signal transmission system which is proceeded in the mitochondria, and prevents apoptosis with its role by promoting the activation of anti-apoptotic signal factors. Moreover, TUDCA suppresses endoplasmic reticulum stress (ER-stress), thereby protecting cells in damaged tissue.

In spite of continual studies on the effect of TUDCA, a cell therapy product using TUDCA has not been developed. Particularly, it was not found out whether TUDCA has excellent angiogenesis and revascularization effects, repairs senescent stem cells, and promotes bioactivity of angiogenic stem cells. Further, no attempts were made to apply TUDCA for overcoming the obstacles to conventional stem cell therapy, which are limited supply of stem cells, senescence of transplanted stem cells and lower survival rate thereof in ischemic tissue, degradation of differentiation into blood vessels, etc.

SUMMARY OF INVENTION

The present inventors tried to develop a novel cell therapy product which enables to improve senescence of stem cells and dysfunction caused thereby, which are problems of previous stem cell therapy, and enhance the functions of stem cells. As a result, the present inventors treated stem cells with tauroursodeoxycholic acid (TUDCA), and confirmed mobilization of angiogenic stem cells from bone marrow, differentiation into progenitor cells, inhibition of senescence occurring in proliferation of stem cells, and enhancement of functions of stem cells, thereby completing the present invention which relates to a process and a novel cell therapy product, which are capable of applying to ischemic diseases.

It is an object of the present invention to provide a process for promoting migration, inducing differentiation, or inhibiting senescence of a stem cell, including treating the stem cell isolated from a living body with TUDCA or a pharmaceutically acceptable salt thereof.

It is another object of the present invention to provide a process for treating an ischemic disease.

It is yet another object to provide a stem cell cellular therapeutic supplementary agent.

The present invention provides a process for promoting migration, inducing differentiation, or inhibiting senescence of a stem cell including TUDCA or a pharmaceutically acceptable salt thereof, thereby effectively improving disadvantages of previous stem cell therapy, which are related to lack of supply of stem cells, inaccurate migration to target organs, lower survival rate in tissue. Also, the present invention can be effectively applied to a method for treating ischemic diseases and as a novel stem cell cellular therapeutic supplementary agent.

BRIEF DESCRIPTION OF DRAWINGS

FIG. 1a illustrates a result of confirmation of adhesion and dissociation capabilities after culturing angiogenic stem cells in bone marrow stromal cells, in order to confirm dissociation of angiogenic stem cells from bone marrow stromal cells. FIG. 1b illustrates a result of confirmation of adhesion capability of angiogenic stem cells which are cultured in bone marrow stromal cells after treatment with TUDCA. FIG. 1c illustrates a result of confirmation of dissociation capability of angiogenic stem cells which are cultured in bone marrow stromal cells after treatment with TUDCA.

FIGS. 2a and 2b illustrates a result of confirmation of mRNA expression of cell adhesion factors associated with cell adhesion. The expression of ICAM, Jagged1, N-cadherin, LFA1, and c-kit, which are cell adhesion factors of angiogenic stem cells, is confirmed after treatment with TUDCA.

FIG. 3a illustrates a result of confirmation of migration capability of angiogenic stem cells treated with TUDCA. FIG. 3b illustrates a result of confirmation of mobilization capability of angiogenic stem cells from bone marrow to peripheral blood over time when TUDCA is orally administered to mice.

FIG. 4a illustrates a result of confirmation of distribution of angiogenic stem cells in peripheral blood, after TUDCA is orally administered to mice. FIG. 4b illustrates a result of confirmation of distribution of angiogenic stem cells in peripheral blood over time, after TUDCA (10 mg/kg) is orally administered to mice. FIG. 4c illustrates a result of confirmation of distribution of leukocytes (WBC), lymphocytes (LY), monocytes (MO), and granulocytes, after TUDCA (10 mg/kg) is orally administered to mice for 3 days. FIG. 4d illustrates a result of confirmation of EPC properties. FIG. 4e illustrates a result of confirmation of the effect of TUDCA in $CD34^+HSC$ differentiation into the EPC lineage. FIG. 4f illustrates a result of confirmation whether TUDCA activates Akt of $CD34^+$ HSC.

FIG. 5a illustrates a result of confirmation of integration capability of angiogenic stem cells into human arterial endothelial cells (HAECs) upon treatment with TUDCA, through tube formation assay. FIG. 5b illustrates a result of quantifying the result of FIG. 5a based on the number of tubes. FIG. 5c illustrates an image showing that angiogenic stem cells are integrated intoarterial endothelial cells forming tubes. Red arrows indicate angiogenic stem cells. FIGS. 5d and 5e each illustrates mRNA expression levels of cell adhesion factors in HAECs and EPCs.

FIGS. 6a-6d illustrate a result of confirmation of bioactivity in angiogenic stem cells, enhanced by TUDCA. FIG. 6a illustrates a result of confirmation of proliferation capability of angiogenic stem cells upon treatment with various concentrations of TUDCA. FIG. 6b illustrates a result of confirmation of infiltration capability of angiogenic stem cells upon treatment with TUDCA (50 μM). FIGS. 6c and 6d illustrate a result of confirmation of tube forming capability of angiogenic stem cells upon treatment with various concentrations of TUDCA and qualification thereof.

FIGS. 7a-7e illustrate a result of confirmation of TUDCA's functions using hindlimb ischemia animal models. After preparing hindlimb ischemia animal models, TUDCA (20 mg/kg) was orally administered to the models every day. FIG. 7a illustrates a result of confirmation of blood flow improvement over time. FIG. 7b illustrates a result of quantifying blood flow improvement. FIG. 7c illustrates a result of confirmation of mobilization capability of angiogenic stem cells, through flow cytometry after removing hindlimb ischemic tissue at day 3 of experiment. FIGS. 7d and 7e illustrate a result of confirmation of angiogenic capability, through immunofluorescent staining, after removing hindlimb ischemic tissue at day 14 of experiment and quantification of capillary and arteriole formation.

FIGS. 8a-8f illustrate a result of confirmation of TUDCA's functions on bone marrow derived angiogenic stem cells, using hindlimb ischemia animal models after transplanting bone marrow of green fluorescent protein (GFP) mice into C57BL/6 mice, in order to confirm whether angiogenic stem cells are derived from bone marrow. After the preparation of bone marrow transplanted mouse hindlimb ischemia animal models, TUDCA (20 mg/kg) was orally administered every day. FIG. 8a illustrates a result of confirmation of blood flow improvement over time. FIG. 8b illustrates a result of quantification of blood flow improvement. FIGS. 8c and 8d illustrate a result of confirmation of angiogenic capability, through immunofluorescent staining, after removing ischemic tissue at day 14 of experiment, and quantification of capillary and arteriole formation. FIG. 8e illustrates a result of confirmation of mobilization capability of bone marrow derived angiogenic stem cells, through immunofluorescent staining, after removing hindlimb ischemic tissue at day 3 of experiment, and quantification thereof. FIG. 8f illustrates a result of confirmation of differentiation of bone marrow derived angiogenic stem cells into vascular endothelial cells, through immunofluorescent staining, after removing hindlimb ischemic tissue at day 14 of experiment, and quantification thereof.

FIGS. 9a-9c illustrate a result of confirmation of effect of oral administration of TUDCA (5 mg/kg) to healthy human subjects for 3 days. FIG. 9a illustrates a result of confirmation of distribution of angiogenic stem cells present in peripheral blood over time, using an angiogenic stem cell marker. FIG. 9b illustrates a result of confirmation of colony forming capability of angiogenic stem cells from peripheral blood monocytes, after treatment with TUDCA. FIG. 9c illustrates a result of confirmation of distribution of lymphocytes and granulocytes in peripheral blood, after treatment with TUDCA.

FIG. 10a illustrates a result of confirmation of senescence recovery through (3-galactosidase staining, after treating TUDCA to senescent angiogenic stem cells due to repeated passages. FIG. 10b illustrates a result of quantification of the result of FIG. 10a. FIG. 10c illustrates a result of confirmation of expression of nitric oxide which is critical to the functions of angiogenic stem cells and expression of reactive oxygen species associated with senescence, when treating TUDCA with senescent angiogenic stem cells.

FIGS. 11a-11g illustrate a result of confirmation of the effect, as a cell therapy product, of senescent angiogenic stem cells due to repeated passages, which are treated with TUDCA and transplanted into mouse hindlimb ischemia models. FIG. 11a illustrates a result of confirmation of blood flow improvement over time after transplantation of senescent angiogenic stem cells treated with TUDCA. FIG. 11b illustrates a result of quantification of blood flow improvement. FIG. 11c illustrates a result of confirmation of capillary angiogenic capability, through immunofluorescent staining, after removing ischemic tissue at day 28 of experiment, and quantification thereof. FIG. 11d illustrates a result of confirmation of arteriole angiogenic capability, through immunofluorescent staining, after removing ischemic tissue at day 28 of experiment, and quantification thereof. FIG. 11e illustrates a result of confirmation of angiogenic capability of alpha smooth muscle actin (α-SMA) expression blood vessels, through immunofluorescent staining, after removing ischemic tissue at day 28 of experiment, and quantification thereof. FIG. 11f illustrates a result of confirmation of secretion of angiogenic cytokines, FGF2, HGF, and SDF-la secreted from angiogenic stem cells into which ischemic tissue removed from ischemic tissue are transplanted, at day 3 of experiment, through immunofluorescent staining. FIG. 11g illustrates a result of confirmation of secretion amounts of angiogenic cytokines by removing ischemic tissue into which angiogenic stem cells are transplanted at day 3 of experiment, through western blotting.

BEST MODE FOR CARRYING OUT THE INVENTION

Hereinafter, the present invention will be described in detail.

According to an aspect of the present invention, there is provided a process for promoting migration, inducing differentiation, or inhibiting senescence of a stem cell, including treating the stem cell isolated from a living body with tauroursodeoxycholic acid (TUDCA) or a pharmaceutically acceptable salt thereof.

In the process according to the present invention, the TUDCA may be present in the form of various salts, pharmaceutically acceptable salts, for example, in the form of alkali metal salts including sodium or potassium, and preferably including TUDCA.

As used herein, the term "stem cells" refer to cells capable of differentiating into at least two types of cells while having self-replicating capability, and may be classified as totipotent stem cells, pluripotent stem cells, and multipotent stem cells.

The stem cells of the present invention may be selected properly without any limitation according to purposes, and be derived from adult cells of all the known tissue or cells obtained from mammals, for example, from bone marrow, umbilical cord blood, placenta (or placental tissue cells), or adipose tissue (adipose tissue cells).

For example, the stem cells may be obtained without any limitation from bone marrow, adipose tissue, muscular tissue, ex vivo cultured autologous mesenchymal stem cells, allogenic mesenchymal stem cells, umbilical cord blood, embryonicyolk sac, placenta, umbilical cord, periosteum, skin from fetuses and adolescence, and blood. The stem cells may be derived from fetuses, newborns, or adults.

According to an embodiment of the present invention, the stem cells may be selected from the group consisting of bone marrow stem cells, endothelial progenitor cells (EPCs), endothelial colony forming cells (ECFCs), vasculogenic progenitor cells (VPCs), mesenchymal stem cells, embryonic stem cells, myoblasts, and cardiac stem cells, preferably be bone marrow stem cells, EPCs, ECFCs, or VPCs, and more preferably bone marrow stem cells, or EPCs.

As used herein, the term "migration" means that cells are positioned at a target site. The term "migration ability" used herein in connection with stem cells may be indicated with a chemotactic index. Preferably, stem cells treated by the process according to the present invention have higher migration property (i.e., higher chemotactic index), compared with non-treated cells, in a TUDCA concentration-dependent manner.

As used herein, the term "differentiation induction" includes not only complete differentiation induction of stem cells into specific cells but also formation of embryonic bodies formed in an intermediate stage before complete differentiation of stem cells into specific cells.

In the present invention, differentiation induction includes not only inducing differentiation of stem cells into specific cells, when the stem cells are directly treated with TUDCA, but also inducing differentiation using stem cells with differentiation potential increased by the direct treatment with TUDCA.

For example, the differentiation of the present invention may induce angiogenesis.

As used herein, the term "angiogenesis" refers to a process through which new blood vessels are formed, i.e., new blood vessels being generated and differentiated into cells, tissue, or organs.

In the present invention, angiogenesis includes vascular regeneration, vascular repair, and vascular differentiation, which are involved in the formation of new blood vessels, in addition to activation, migration, and proliferation of endothelial cells, reformation of matrix, and stabilization of cells.

In order to repair ischemic tissue caused by vascular damage, the formation of new blood vessels is necessary. The proliferation of preexisting vascular endothelial cells alone is insufficient for angiogenesis and repair. Thus, it is significant in the angiogenesis process to mobilize angiogenic stem cells derived from bone marrow to an ischemic site to be involved in vascular recovery.

The process according to the present invention promotes mobilization of angiogenic stem cells from bone marrow to ischemic tissue, increases integration capability with vascular endothelial cells, and increases differentiation potential into blood vessels.

As used herein, the term "senescence" refers to a halt or significant delay in cell growth and cell division against diverse internal or external stress (e.g., high concentration of oxygen in continuous passages and in vitro culture), from which stem cells suffer.

According to an embodiment of the present invention, the TUDCA may be included in a concentration of 1 to 200 μM, preferably 1 to 100 μM, more preferably 20 to 60 μM, and most preferably 50 μM.

Also, the present invention may treat stem cells with TUDCA, followed by co-culture for 10 hours or more and 15 hours or less.

According to the present invention, TUDCA enhances mobilization capability which dissociates angiogenic stem cells from bone marrow stromal cells and delivers angiogenic stem cells to peripheral blood. As the number of angiogenic stem cells in peripheral blood increases, expression levels of CD34, CD31, and c-kit, which are angiogenic stem cell markers, increase. Further, the angiogenic stem cells mobilized from bone marrow are integrated into vascular endothelial cells preexisting in damaged tissue, leading to angiogenesis via interaction. As expression levels of fibroblast growth factor 2 (FGF2), hepatocyte growth factor (HGF), and stromal cell-derived factor 1α (SDF-1α) increase, angiogenesis and differentiation of stem cells can be promoted.

Also, according to the present invention, TUDCA increases an expression level of nitric oxide and decreases an expression level of reactive oxygen species. Thereby, senescence of stem cells may be inhibited.

According to an aspect of the present invention, there is provided a process for treating an ischemic disease, including administering to a subject a therapeutically effective amount of a composition including, as active ingredients, the following ingredients of (a) a stem cell isolated from a living body; and (b) TUDCA or a pharmaceutically acceptable salt thereof.

According to an embodiment of the present invention, the ischemic disease may be selected from the group consisting of ischemic heart disease, ischemic myocardial infarction, ischemic heart failure, ischemic gastroenteritis, ischemic vascular disease, ischemic ocular disease, ischemic retinopathy, ischemic glaucoma, ischemic kidney failure, ischemic boldness, ischemic stroke, and ischemic limb disease, preferably selected from the group consisting of ischemic heart disease, ischemic myocardial infarction, ischemic heart failure, ischemic gastroenteritis, ischemic vascular disease, ischemic stroke, and ischemic limb disease, and more preferably ischemic stroke, and ischemic hindlimb disease.

According to an embodiment of the present invention, the stem cell may be selected from the group consisting of a bone marrow stem cell, an endothelial progenitor cell (EPC), an endothelial colony forming cell (ECFC), a vasculogenic progenitor cell (VPC), a mesenchymal stem cell, an embryonic stem cell, a myoblast, and a cardiac stem cell, preferably a bone marrow stem cell, an EPC, an ECFC or a VPC, and more preferably a bone marrow stem cell or an EPC.

According to an embodiment of the present invention, the composition may increase migration promotion, differentiation induction, or senescence inhibition of the stem cell.

According to an embodiment of the present invention, the TUDCA may be included in a concentration of 1 to 200 µM, preferably 1 to 100 µM, more preferably 20 to 60 µM, and most preferably 50 µM.

As used herein, the term "therapeutically effective amount" refers to an amount of the composition sufficient to achieve therapeutic effect or activity against the diseases.

When the composition of the present invention is prepared as a pharmaceutical composition, the composition may further include appropriate carriers, excipients, and diluents, which are commonly used in the preparation of pharmaceutical composition.

Also, the composition of the present invention may be formulated according to general methods into oral dosage forms including powders, granules, tablets, capsules, suspensions, emulsions, syrups, or aerosols; external dosage forms; suppository; or sterile injection solution. As appropriate formulations known in the art, those disclosed in the reference (Remington's Pharmaceutical Science, recent edition, Mack Publishing Company, Easton Pa.) may be preferably used. Examples of carriers, excipients, and diluents to be included in the composition may include lactose, dextrose, sucrose, sorbitol, mannitol, xylitol, erythritol, maltitol, starch, acacia gum, alginate, gelatin, calcium phosphate, calcium silicate, cellulose, methyl cellulose, microcrystalline cellulose, polyvinyl pyrrolidone, water, methylhydroxy benzoate, propylhydroxy benzoate, talc, magnesium stearate, and a mineral oil. When the composition is formulated, diluents or excipients are used including fillers, extenders, binders, humectants, disintegrators, or surfactants, which are commonly used. Examples of solid formulations for oral administration may include tablets, pills, powders, granules, or capsules. The solid formulations may be prepared by adding to the composition at least one excipient, for example, starch, calcium carbonate, sucrose, lactose, or gelatin. In addition to the simple excipient, a lubricant such as magnesium stearate or talc may also be used. Examples of liquid formulations for oral administration may include suspensions, internal use liquids, emulsions, or syrups. In addition to the simple diluents such as water or liquid paraffin, various excipients, for example, humectants, sweeteners, fragrants, or preservatives may also be included. Examples of formulations for parenteral administration may include sterilized aqueous solutions, non-aqueous solvents, suspensions, emulsions, lyophilized preparations, and suppositoriums.

Examples of non-aqueous solvents and suspensions may include propylene glycol, polyethylene glycol, vegetable oil such as olive oil, injectable ester such as ethylolate. Suppositories may include witepsol, macrogol, tween 61, cacao butter, laurin butter, or glycerinated gelatin.

As used herein, the term "administration" means providing the composition to a subject through any appropriate way.

A preferable dosage of the composition of the present invention may vary depending on the subject's health condition and body weight, severity of disease, formation types, administration routes and period, etc., but may be appropriately chosen by one skilled in the art. In order to achieve preferred effects, the daily dosage of the composition of the present invention may be between 1 to 10000 mg/kg. The composition may be administered once or a few times daily.

The composition of the present invention may be administered via various routes. Every administration route may be expected, and for example, oral, rectal or intravenous, muscular, subcutaneous, intrauterine, or intracerebroventricular injection may be used.

According to an aspect of the present invention, there is provided a stem cell cellular therapeutic supplementary agent or cellular therapeutic supplementary agent including TUDCA or a pharmaceutically acceptable salt thereof, as an active ingredient.

As used herein, the term "stem cell cellular therapeutic supplementary agent" refers to a formulation which can be used adjunctively for enhancing the effect of stem cell therapy products, which are generally used in the art. The use of the agent of the present invention can promote differentiation and inhibit senescence of stem cells in stem cell therapy products, thereby increasing the effect of the therapy products.

As used herein, the term "cellular therapeutic agent" or "cellular therapeutic supplementary agent" refers to a pharmaceutical used for treating, diagnosing, or preventing diseases through a series of actions including changing biological properties of cells by proliferating or selecting living autologous, allogenic, or xenogenic cells in vitro or using other ways, in order to restore functions of cells and tissue. Particularly, the stem cell therapy product may be classified as embryonic stem cell therapy product and adult stem cell therapy product.

The stem cell cellular therapeutic supplementary agent may be administered to a subject via any general administration route as long as it can reach target tissue.

The administration route of the stem cell cellular therapeutic supplementary agent may be administered intraperitoneally, intravenously, intramuscularly, or subcutaneously, but is not limited thereto.

Also, the stem cell cellular therapeutic supplementary agent may be administered using any device which can deliver an active ingredient to a target cell. The stem cell cellular therapeutic supplementary agent may be administered with a pharmaceutical carrier which is generally used for stem cell therapy. Examples of the carrier may include physiological saline solutions.

Hereinafter, the following examples are provided for illustrative purposes only, and those skilled in the art will appreciate that the present invention is not limited to the scope of the examples.

Example 1: Confirmation on TUDCA's Capabilities of Dissociating Angiogenic Stem Cells from Bone Marrow Stromal Cells and Mobilizing Angiogenic Stem Cells to Peripheral Blood When ischemic damage occurs, for vascular repair, a process in which angiogenic stem cells integrated with bone marrow stromal cells are dissociated from bone marrow and transported to ischemic tissue first occurs in the vascular repair mechanism. In order to confirm a change in dissociation of angiogenic stem cells from bone marrow stromal cells by TUDCA, CD34$^+$ cells stained with CM-DiI (staining red), which were treated with TUDCA (0, 50, 100 μM), were incubated for 1 hour on glass slides in which bone marrow stromal cells were seeded. The number of CD34$^+$ cells adhered to or dissociated from bone marrow stromal cells was counted by a fluorescence microscope (FIGS. 1a, 1b, and 1c). AMD3100, a CXCR4 antagonist, was used as a positive control. As a result, it was confirmed that in the group treated with TUDCA, the number of CD34$^+$ cells adhered to the stromal cells significantly decreased, and the number of CD34$^+$ cells dissociated from the stromal cells significantly increased, as compared with the control.

Based thereon, a change in mRNA expression of cell adhesion factors involved in cell adhesion was confirmed. After treating CD34$^+$ cells with TUDCA (50 μM) for 5 hours, mRNA expression of ICAM, Jagged', N-cadherin, LFA1, and c-kit, which are involved in cell adhesion, was confirmed. As a result, it was found that the expression of cell adhesion factors significantly decreased by TUDCA (FIGS. 2a and 2b).

In order to confirm mobilization capability of angiogenic stem cells, which were dissociated from bone marrow stromal cells, to peripheral blood, CD34$^+$ hematopoietic stem cells (HSCs) were treated with various concentrations of TUDCA (0, 10, 50, 100 μM), to confirm the cell migration capability by trans-well assay. As a result, it was confirmed that the migration capability of CD34$^+$ cells significantly increased in a TUDCA concentration-dependent manner (FIG. 3a). Based on the result, TUDCA (10 mg/kg) was orally administered to C57BL/6 mice, and the number of angiogenic stem cells (CD34$^+$/Sca1$^+$) in peripheral blood were analyzed by FACS analysis over time (at day 0, 1, 3). As a result, it was confirmed that the number of angiogenic stem cells in peripheral blood of mice significantly increased when TUDCA was orally administered (FIG. 3b).

Example 2: Confirmation on Cell Population Mobilized by TUDCA to Peripheral Blood When TUDCA was orally administered, a variety of cell populations are mobilized to peripheral blood. After orally administering TUDCA to mice, the cell populations were analyzed by Hill's assay. As a result, it was confirmed that the number of angiogenic stem cells increased in TUDCA concentration and time-dependent manner (FIGS. 4a and 4b). In order to confirm side effects caused by mobilization of cell populations associated with immunity and inflammation, other than angiogenic stem cells, upon treatment with TUDCA, the change in the number of leukocytes, lymphocytes, monocytes, and granulocytes in peripheral blood was confirmed by complete blood cell (CBC) count. As a result, it was confirmed that the number of granulocytes involved in inflammatory response significantly decreased (FIG. 4c). Also, it was confirmed that granulocytes are EPCs by confirming the uptake of acetyl-LDL and FITC-isolectin B4 (FIG. 4d).

Meanwhile, in order to clarify the impact of TUDCA on CD34$^+$ HSC differentiation into the EPC lineage, the EPC colony forming capability of CD34$^+$ HSCs was examined. As a result, it was confirmed that the EPC colony forming capability was enhanced by TUDCA (FIG. 4e). Further, as Akt activation via PI3-kinase increases differentiation of CD34$^+$ HSCs into the EPC lineage, it was examined whether TUDCA activates Akt in CD34$^+$ HSC. As a result, it was confirmed that TUDCA increased Akt phosphorylation, and the exposure to LY294002, a PI3K inhibitor, inhibited TUDCA-mediated CD34$^+$ HSC differentiation into the EPC lineage (FIG. 4f).

Example 3: Confirmation on TUDCA's Capability of Integrating Angiogenic Stem Cells with Vascular Endothelial Cells It is the most significant process in the vascular recovery mechanism that angiogenic stem cells mobilized from bone marrow are integrated with vascular endothelial cells pre-existing in damaged tissue, to generate new blood vessels through interaction. Human arterial endothelial cells (HAECs) were mixed with angiogenic stem cells, and then the integration capability between the two cells was examined by tube formation assay. As a result, it was confirmed that the tube formation capability significantly increased depending on treatment with TUDCA (50 μM) and mixture with angiogenic stem cells (FIGS. 5a, 5b, and 5c).

Further, as the first step of integration with vascular endothelial cells is cell adhesion, mRNA expression levels of cell adhesion molecules in HAECs and EPCs were examined. As a result, it was confirmed that TUDCA significantly increased the expression levels of CD44, N-cadherin, c-kit, and LFA1 in HAECs and the expression levels of CD44, Jagged-1, N-cadherin, VLA5, CXCR4, c-kit, and Notch in EPCs (FIGS. 5d and 5e).

Example 4: Confirmation on Biological Activity of Angiogenic Stem Cells, Enhanced by TUDCA In order to confirm that the treatment with TUDCA involves enhancement of biological activity functions of angiogenic stem cells in addition to enhancement of mobilization and migration capabilities of angiogenic stem cells from bone marrow to peripheral blood and ischemic tissue, angiogenic stem cells were treated with different concentrations (0, 10, 50, 100 μM) of TUDCA. Then, various biological activity functions were evaluated. When angiogenic stem cells were treated with 50 μM of TUDCA, the proliferation and infiltration capabilities of angiogenic stem cells most significantly increased (FIGS. 6a and 6b). In order to confirm vascular differentiation potential, tube-forming capability was examined. As a result, it was confirmed that tube-forming capability of angiogenic stem cells significantly increased in a TUDCA concentration-dependent manner (FIGS. 6c and 6d).

Example 5: Confirmation on Vascular Repair Capability of TUDCA Using Mouse Hindlimb Ischemia Model TUDCA was applied to mouse disease models based on the above experiments, to verify the effects. Mouse hindlimb ischemia model, which is one of the disease animals, for verifying vascular repair capability was prepared. Thereafter, 20 mg/kg of TUDCA was orally administered to mice every day, to confirm vascular repair capability over time. As a result of confirming blood flow improvement by TUDCA using Laser Doppler perfusion imaging assay (LDPI assay), it was found that blood flow improvement significantly increased in the group to which TUDCA was orally administered (FIGS. 7a and 7b). In order to confirm whether angiogenic stem cells were mobilized by TUDCA to hindlimb ischemic tissue, hindlimb ischemic tissue was removed 3 days after the preparation of the hindlimb ischemia models, and flow cytometry was performed using an angiogenic stem cell marker. As a result, it was confirmed that the number of angiogenic stem cells in ischemic tissue increased in the group to which TUDCA was orally administered (FIG. 7c). In order to confirm angiogenesis by TUDCA, hindlimb ischemic tissue was removed 14 days after the preparation of the hindlimb ischemia models and subjected to immunofluorescent staining, to verify capillary density and arteriole density. As a result, it was confirmed that the number of capillaries and arterioles significantly increased in the group treated with TUDCA (FIGS. 7d and 7e).

Example 6: Confirmation on Vascular Repair Capability of TUDCA in Mouse Hindlimb Ischemia Animal Model Using GFP Bone Marrow-Transplanted Mice It is known that angiogenic stem cells are mainly present in bone marrow, but they are present in different tissues than bone marrow. In order to confirm whether angiogenic stem cells are derived from bone marrow by TUDCA and involved in vascular repair mechanism, bone marrow was isolated from green fluorescent protein (GFP) mice and transplanted into C57BL/6. Once bone marrow transplantation (BMT) mice are thus prepared, chimeric mice which show green fluorescence only for bone marrow cells are obtained. After preparing hindlimb ischemia animal models using GFP-BMT mice, TUDCA (20 mg/kg) was orally administered to verify vascular repair capability. As a result of verification on blood flow improvement by TUDCA using Laser Doppler perfusion imaging assay (LDPI assay), it was found that blood flow was significantly improved in the group to which TUDCA was orally administered (FIGS. 8a and 8b). In order to confirm angiogenesis by TUDCA, hindlimb ischemic tissue was removed 14 days after the preparation of the hindlimb ischemia models and subjected to immunofluorescent staining, to verify capillary and arteriole density. As a result, it was confirmed that the number of capillaries and arterioles significantly increased in the group treated with TUDCA (FIGS. 8c and 8d). In order to confirm whether angiogenic stem cells were mobilized by TUDCA from bone marrow to hindlimb ischemic tissue, mobilization capability of angiogenic stem cells was examined by immunofluorescent staining using a bone marrow marker GFP, an angiogenic stem cell marker c-kit, a vascular marker ILB4, into which hindlimb ischemic tissue removed from the hindlimb ischemia models was transplanted 3 days after the preparation. As a result, it was confirmed that the number of angiogenic stem cells derived from bone marrow into ischemic tissue significantly increased in the group to which TUDCA was orally administered (FIG. 8e). In order to examine whether angiogenic stem cells mobilized by TUDCA from bone marrow differentiate into new blood vessels in hindlimb ischemic tissue, vascular differentiation potential of angiogenic stem cells was examined, through immunofluorescent staining and morphological analysis, using a bone marrow marker GFP, a marker of vascular differentiation VEGFR, a vascular marker ILB4, into which hindlimb ischemic tissue removed from the hindlimb ischemia models was transplanted 14 days after the preparation. As a result, it was confirmed that in the group to which TUDCA was orally administered, bone marrow-derived angiogenic stem cells in ischemic tissue were differentiated into vascular endothelial cells and that the number thereof significantly increased (FIG. 8f).

Example 7: Confirmation on Cell Population Mobilized to Peripheral Blood Upon Oral Administration of TUDCA to Healthy Subjects Upon oral administration of TUDCA to healthy subjects, angiogenic stem cells and various cell populations, which were mobilized to peripheral blood, were confirmed and differentiation potential into functional endothelial progenitor cells was verified using peripheral blood. 5 mg/kg of TUDCA was orally administered to healthy subjects for 3 days, and the expression of angiogenic stem cell markers was examined. As a result, it was confirmed that the expression of angiogenic stem cell markers CD34, CD31, and c-kit significantly increased (FIG. 9a). As a result of confirmation of cell colony forming capability of angiogenic stem cells in peripheral blood through endothelial progenitor cell-colony forming assay (EPC-CFA), it was found that colony forming capability significantly increased in the group to which TUDCA was orally administered (FIG. 9b). As a result of confirmation of a change in distribution of various cell populations after oral administration of TUDCA, it was found that the distribution of granulocytes involved in inflammatory response significantly decreased (FIG. 9c).

Example 8: Confirmation on Senescence Inhibition Capability of TUDCA Upon In Vitro Expansion of Angiogenic Stem Cells In order to use stem cells as a stem cell therapy product, it is important to obtain a sufficient number of stem cells in a healthy state. However, upon in vitro expansion of stem cells for obtaining a sufficient number of stem cells, repeated passages cause senescence of stem cells. In order to resolve this problem, angiogenic stem cells subjected to repeated passages (passages 13 to 16) were treated with TUDCA, to verify senescence inhibition. Senescent angiogenic stem cells were treated with TUDCA and subjected to β-galactosidase staining capable of confirming senescence, to confirm senescence recovery. As a result, it was confirmed that the number of β-galactosidase positive cells significantly increased in the group treated with TUDCA (FIGS. 10a and 10b). In order to confirm through what mechanism TUDCA inhibits senescence, as a result of confirming expression amounts of nitric oxide which is critical to the function of angiogenic stem cells and of reactive oxygen species which are critical to the senescence process, it was confirmed that in the angiogenic stem cells treated with TUDCA, the expression amount of nitric oxide significantly increased and the expression amount of reactive oxygen species significantly decreased (FIG. 10c).

Example 9: Verification on Function of Novel Stem Cell Therapy Product Using TUDCA and Angiogenic Stem Cells in Hindlimb Ischemia Animal Model In order to verify the effects of novel stem cell therapy products with improved functions by treating TUDCA to senescent angiogenic stem cells subjected to repeated passages, mouse hindlimb ischemia animal models were prepared. Thereafter, novel angiogenic stem cell therapy products which treated TUDCA to senescent angiogenic stem cells were transplanted into the mouse hindlimb ischemia animal models, to confirm the therapeutic effect. Then, blood flow improvement was examined using Laser Doppler perfusion imaging assay. As a result, it was confirmed that blood flow improvement significantly increased in the group into which angiogenic stem cells treated with TUDCA were transplanted, as compared with other groups (FIGS. 11a and 11b). In order to confirm angiogenesis by the novel angiogenic stem cell therapy products, hindlimb ischemic tissue was removed 28 days after the preparation of the hindlimb ischemia models and subjected to immunofluorescent staining, to verify the density of capillary, arteriole, and alpha-smooth muscle actin (α-SMA) expression blood vessel. As a result, it was confirmed that the number of capillaries, arterioles, and alpha-smooth muscle actin (α-SMA) expression blood vessels significantly increased in the group into which angiogenic stem cells treated with TUDCA were transplanted (FIGS. 11c, 11d, and 11e). In order to confirm expression amounts of angiogenic cytokines secreted from angiogenic stem cells which were transplanted into ischemic tissue, each ischemic tissue into which angiogenic stem cells were transplanted was removed and subjected to immunofluorescent staining and western blotting, to confirm expression amounts of angiogenic cytokines. As a result, it was confirmed that expression amounts of angiogenic cytokines FGF2, HGF, and SDF-1a increased in the group into which angiogenic stem cells treated with TUDCA were transplanted, as compared with other groups (FIGS. 11f and 11g).

What is claimed is:

1. A process for promoting migration, inducing differentiation, or inhibiting senescence of endothelial progenitor cells (EPCs), the process comprising:
   treating endothelial progenitor cells isolated from a living body with tauroursodeoxycholic acid (TUDCA) or a pharmaceutically acceptable salt thereof.

2. The process of claim 1, wherein the TUDCA is treated in a concentration of 1 to 200 μM.

3. The process of claim 1, wherein the TUDCA increases an expression level of at least one selected from the group consisting of CD34, CD31, and c-kit in the endothelial progenitor cells.

4. The process of claim 1, wherein the TUDCA increases an expression level of at least one selected from the group consisting of fibroblast growth factor 2 (FGF2), hepatocyte growth factor (HGF), and stromal cell-derived factor 1α (SDF-1α), which are angiogenic cytokines in the endothelial progenitor cells.

5. The process of claim 1, wherein the TUDCA increases an expression level of nitric oxide (NO) and decreases an expression level of reactive oxygen species in the endothelial progenitor cells.

* * * * *